(12) United States Patent
Mendels et al.

(10) Patent No.: US 11,256,998 B2
(45) Date of Patent: Feb. 22, 2022

(54) PATTERN RECOGNITION AND PREDICTION USING A KNOWLEDGE ENGINE

(71) Applicant: Intel Corporation, Santa Clara, CA (US)

(72) Inventors: Omri Mendels, Tel Aviv (IL); Boris Kodner, Beer-Sheva (IL); Ariel Benou, Beer-Sheva (IL); Oded Vainas, Petah Tiqwa (IL); Avi Samoucha, Tel Aviv (IL); Tali Zvi, Givataim (IL)

(73) Assignee: Intel Corporation, Santa Clara, CA (US)

( * ) Notice: Subject to any disclaimer, the term of this patent is extended or adjusted under 35 U.S.C. 154(b) by 1386 days.

(21) Appl. No.: 15/414,387

(22) Filed: Jan. 24, 2017

(65) Prior Publication Data
US 2018/0211175 A1 Jul. 26, 2018

(51) Int. Cl.
*G06N 5/04* (2006.01)
*G16H 10/60* (2018.01)
*G16H 50/70* (2018.01)
*G16H 50/20* (2018.01)
*G16H 40/67* (2018.01)
(Continued)

(52) U.S. Cl.
CPC .............. *G06N 5/048* (2013.01); *G06N 5/04* (2013.01); *G06N 7/005* (2013.01); *G16H 10/60* (2018.01); *G16H 20/30* (2018.01); *G16H 40/67* (2018.01); *G16H 50/20* (2018.01); *G16H 50/70* (2018.01); *G06Q 10/06314* (2013.01)

(58) Field of Classification Search
CPC ....................................... G06N 5/04

USPC .......................................................... 706/46
See application file for complete search history.

(56) References Cited

U.S. PATENT DOCUMENTS

| 6,614,348 B2 | 9/2003 | Ciccolo et al. |
| 2014/0018638 A1 | 1/2014 | Chatterjee |
| 2015/0019710 A1 | 1/2015 | Shaashua et al. |

FOREIGN PATENT DOCUMENTS

EP 2750098 7/2014

OTHER PUBLICATIONS

Nazerfard et al ("Discovering Temporal Features and Relations of Activity Patterns" 2010) (Year: 2010).*
(Continued)

*Primary Examiner* — Lut Wong
(74) *Attorney, Agent, or Firm* — Schwegman Lundberg & Woessner, P.A.

(57) ABSTRACT

Various systems and methods for processing activity data with a knowledge engine to generate actionable insights for a human subject are described. These actionable insights may include identifying a most likely action given a particular state of the human subject, identifying a most likely state in which the human subject performs a particular activity, or identifying anomalies in human activity patterns. In an example, an electronic processing system operates the knowledge engine with operations that: identify patterns of activity using clustering of events, identify meaningful patterns of activity from the patterns of activity based on co-occurrence of characteristics for respective events, rank the identified meaningful patterns of activity based on confidence and support of respective patterns to occur for a human subject, and generate a personalization action (such as an action for a software application) based on the ranked, identified meaningful patterns of activity.

25 Claims, 10 Drawing Sheets

(51) Int. Cl.
    *G16H 20/30*     (2018.01)
    *G06N 7/00*     (2006.01)
    *G06Q 10/06*     (2012.01)

(56) References Cited

OTHER PUBLICATIONS

Cao ("An Integrated Framework for Human Activity Recognition" 2012) (Year: 2012).*

Unger et al. ("Towards latent context-aware recommendation systems" 2016) (Year: 2016).*

Pessemier et al. ("Context-aware recommendations through context and activity recognition in a mobile environment" 2013) (Year: 2013).*

"Devices Used for Medical Applications", Vandrico Inc., [Online]. Retrieved from the Internet: URL: http://vandrico.com/wearables/device-categories/application/medical, (Accessed on: Dec. 1, 2016), 11 pgs.

Ali, Raza, "Pattern Mining for Routine Behaviour Discovery in Pervasive Healthcare Enviroments", International Conference on Information Technology and Applications in Biomedicine, (May 2008), 4 pgs.

Fahim, Muhammad, "ATHENA: A Personalized Platform to Promote an Active Lifestyle and Wellbeing Based on Physical, Mental and Social Health Primitives", Journal of Sensors, 14(5), (May 2014), 9313-9329.

Rashidi, Parisa, "Mining and Monitoring Patterns of Daily Routines for Assisted Living in Real World Settings", Proceedings of the 1st ACM International Health Informatics Symposium, (Nov. 2010), 336-345.

Su, Xing, "Activity recognition with smartphone sensors", Tsinghua Science and Technology, 19(3), (Jun. 18, 2014), 235-249.

* cited by examiner

| | NAME | SUPPORT | CONFIDENCE | SCORE |
|---|---|---|---|---|
| 1 | MORNING <-> RUNNING | 9 | 0.90 | 0.51 |
| 2 | MORNING <-> RUNNING <-> WEEKDAY | 7 | 0.70 | 0.41 |
| 3 | MORNING <-> RUNNING <-> TEMPERATURE: MEDIUM (15C-25C) | 6 | 0.60 | 0.38 |
| 4 | MORNING <-> RAIN: NO <-> RUNNING | 6 | 0.60 | 0.38 |
| 5 | RUNNING <-> TEMPERATURE: MEDIUM (15C-25C) | 6 | 0.60 | 0.38 |
| 6 | RAIN: NO <-> RUNNING | 6 | 0.60 | 0.38 |
| 7 | HOME <-> MORNING <-> RUNNING | 5 | 0.50 | 0.32 |

FIG. 5

PATTERN RECOGNITION AND PREDICTION USING A KNOWLEDGE ENGINE

TECHNICAL FIELD

Embodiments described herein generally relate to data modeling and predictive analysis, and in particular, to the identification and evaluation of patterns, correlations, and other data events for use with user-interactive agents that are operated by a human user.

BACKGROUND

With the growing usage of personal electronic devices (such as wearable devices), many types of software applications attempt to provide a personalized user experience by analyzing user data. However, the implementation of personalized software and electronic features is often difficult and costly. For example, personalization features often require acquiring, storing, analyzing and fitting models to data; personalization is commonly repeated per application and per feature; personalization is often domain-specific, and is not portable from one application to another; and, each application or device is typically only aware of the data it is actively collecting.

Personalization is an important feature that is desired in many computing applications. However, existing processing approaches and systems that attempt to implementation personalization, such as with advanced machine learning models, are computationally complex and not appropriate for use cases with personal electronic devices. Many existing approaches are further unable to create personalized insights for individual users based exclusively on the user's own data. As a result, many software applications and electronic devices are unable to fully offer and implement personalization features.

BRIEF DESCRIPTION OF THE DRAWINGS

In the drawings, which are not necessarily drawn to scale, like numerals may describe similar components in different views. Like numerals having different letter suffixes may represent different instances of similar components. Some embodiments are illustrated by way of example, and not limitation, in the figures of the accompanying drawings in which:

FIG. 5 illustrates a ranking of co-occurrences processed with a knowledge engine, according to an example;

DETAILED DESCRIPTION

In the following description, methods, configurations, and related apparatuses are disclosed for generating personalized insights on user behavior, based on a holistic view on user states, actions, and intents. This techniques described herein automatically identify significant patterns in which specific intents come to play at specific states. The techniques described herein may be utilized in a wide variety of fields and types of software applications, including specialized applications operating on personal electronic devices such as wearables and smartphone mobile computing devices.

As discussed in the following examples, the presently disclosed knowledge engine configuration may be used to gather data from various sources, recognize meaningful patterns in user activity over time, and output a list of the most significant patterns to a consuming application, such as a mobile software app). This knowledge engine may process insights and data, to consume discrete temporal events from various sources (e.g., user location, activity, actions, meetings, physiological information etc.) and extract behavioral patterns.

In an example, the knowledge engine performs processing of user events and actions through: (a) co-occurring and consecutive events clustering; (b) meaningful pattern mining; and (c) ranking. Using patterns ranked by significance, the knowledge engine may extract behavioral insights about the user's specific activities. Additionally, pattern mining may be performed on the events metadata to obtain additional understanding of data values, characteristics, and ultimately, insights for personalization.

With use of the techniques described herein, application developers in various fields (fitness, personal assistance, healthcare, education, travel, productivity and more) may use the derived insights to deliver more personalized and context aware features. The techniques described herein may also provide benefits to end users through the improved personalization of software products. Further, in some examples, actionable and personalized data decisions and inferences may be generated from software products, to allow valuable behavior analysis, insights, and notifications to be initiated on behalf of human users.

In contrast to the techniques discussed herein, other personalization engines often employ machine learning models that have a different underlying mechanism than the proposed system. These systems are often domain specific, require data from multiple users, and require larger amounts of training data in order to detect a pattern for a specific user. The system discussed herein assumes a certain model of user behavior that greatly facilitates the discovery of behavioral patterns, and thus reduces the computational complexity and processing resources needed for deriving personalization.

Figure 1:
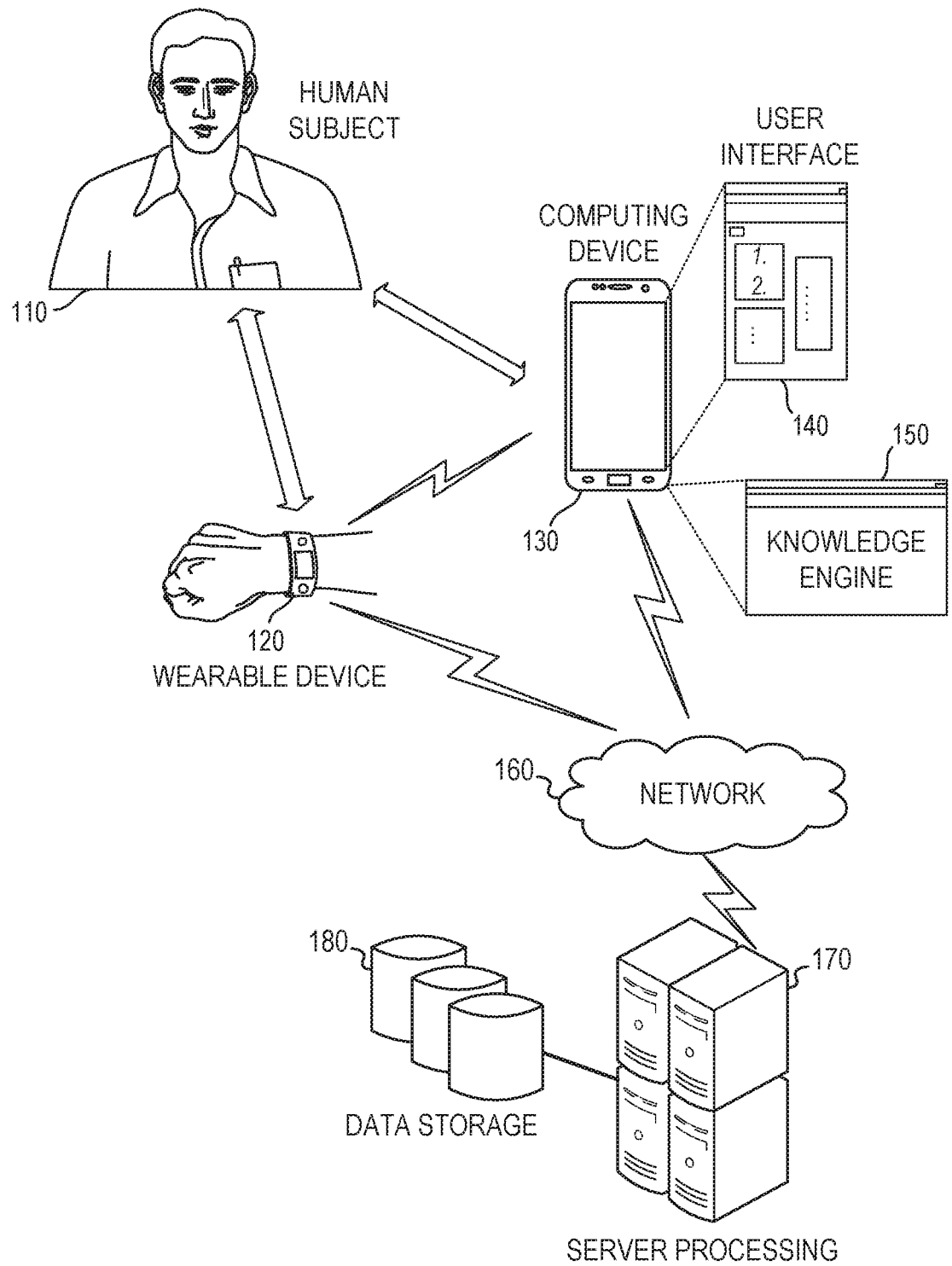
FIG. 1 illustrates a diagram of devices and systems used for collecting, processing, and outputting personalization data with a knowledge engine, according to an example.

FIG. 1 illustrates a diagram of devices and systems used for collecting, processing, and outputting data with use of a knowledge engine 150, according to an example. As shown, a human subject 110 operates one or more electronic devices, such as a computing device 130 and a wearable device 120, which perform automatic and user-controlled electronic functions for data collection and output via such devices. These electronic functions may operate to collect data using one or more integrated or coupled sensors (not shown), based on the activity or location of the human subject 110 or other persons and objects in proximity to the human subject 110.

The specific processing components to enable the operation of the knowledge engine 150 may include processing logic and circuitry implemented by one or more computing devices of the human subject 110, such as executed with the computing device 130. For example, the processing components to implement the knowledge engine 150 may be implemented in computer hardware described below with respect to FIGS. 9 and 10 (e.g., with use of processing circuitry). Other processing circuitry, sensors, communication components, data mediums, and like hardware not depicted in FIG. 1 may be integrated into the computing device 130 or the wearable device 120 to achieve the functionality described herein.

As shown, the computing device 130 executes a user interface 140 to allow interaction and receipt of user content, including the output, selection, and refinement of actionable data outputs (such as through personalization, recommendations, and user indications) from the knowledge engine 150. The computing device 130 may further operate logic or specialized programming (e.g., software code) for the knowledge engine 150 to evaluate the collected data for the human subject 110. The features of the knowledge engine 150 are further described in the following sections, and such features may include aspects of event clustering, pattern mining, pattern ranking, and the initiation of electronic operations and actions in response to identified events and patterns.

The environment of FIG. 1 further depicts the communication of data from the electronic devices (e.g., from the computing device 130 and the wearable device 130) to one or more processing servers 170 via a network (e.g., via wired or wireless communications with a wired or wireless communications network 160). The processing servers 170 may operate to store the data (e.g., data consumed or produced by the knowledge engine 150) in one or more data stores 180. In an example, the processing servers 170 operate to perform event processing and evaluation using the techniques described in the following sections. In another example, the processing servers 170 communicate additional data to the computing device 130 or the wearable device 120 to enable the client devices to perform event clustering, pattern mining, and pattern ranking operations with client-side operations. In either example, the processing servers 170 and the data store 180 may be used to enhance the operational features and the eventual output provided via the user interface 140 and the knowledge engine 150.

Figure 2:
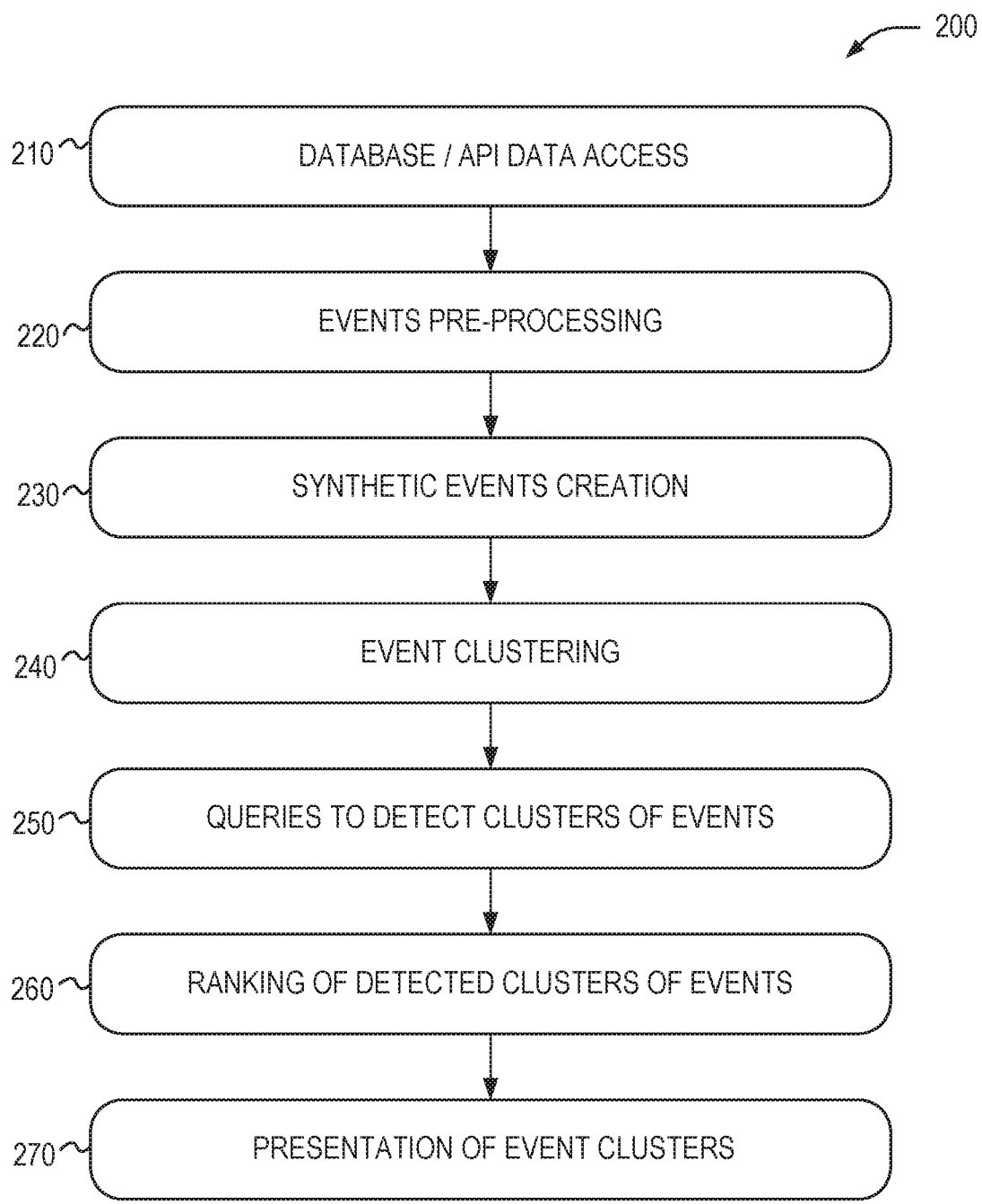
FIG. 2 illustrates a data operation flow for event and pattern processing occurring with a knowledge engine, according to an example.

FIG. 2 illustrates an example data operation flow 200 for event and pattern processing occurring with a knowledge engine. As shown, the data operation flow 200 depicts data operations that may be implemented with software processing actions in a client computing device. It will be understood that other sequences or processing may also be implemented with features of the knowledge engine discussed herein, such as for implementation with a server computing device or with distributed computing devices.

As shown, the data operation flow 200 first starts with the access of data by the knowledge engine from a database or an application programming interface (API) access 210. The knowledge engine may consume data from multiple sources of data, including sources that are internal or external to the client computing device. The operational flow 200 continues with events pre-processing 220. For example, such events pre-processing may be used to change all consumed events (e.g., events indicated from the data provided from the database or API access 210) to a generic form, and to cleanse the data (e.g., remove unneeded or unwanted data fields or values, such as from a particular class of activities) if needed.

The data operation flow 200 may continue with the creation of synthetic events 230, such as with the creation of new events that provide context to the consumed events. The creation of synthetic events 230 may include the creation of "start visit" and "end visit" for detected "visit" events (e.g., a visit by the human user to a specific location), or the creation of "in transit" events for correlated movement (e.g., driving) and visit events. In further examples, the creation of synthetic events 230 may include the creation of events from metadata of original events. For example, two new events, "meet Dan", "meet Rob" may be generated out of a meeting event scheduled between these two participants; likewise, a new event "high calorie burn run" may be generated from a run exercise event that is associated with a specific calorie burn metadata.

The data operation flow 200 continues with events clustering 240, such as data grouping performed from the creation of clusters of events by co-occurrences, consecutive identified events, or the merging of events. The events clustering 240 may be accompanied by operations of various data queries to detect clusters of events 250 (e.g., queries executed with a query engine). The logic to detect the clusters of events may be implemented at the client computing device or at a remote data processing system.

The data operation flow 200 continues with one or more rankings of the detected clusters of events 260. In some examples, the clusters of events may be queried and ranked using a search engine or search algorithm. Finally, a presentation of the clustered events 270 may be generated or outputted. For example, event clustering may be directly displayed to a user with a graphical user interface output, or other forms of output may be provided with use of personalization, decision support, or data output to other models.

Based on the operations of the data operation flow 200, the knowledge engine conducts operations in three primary processing phases in order to extract behavioral patterns: 1) co-occurring and consecutive events clustering; 2) meaningful pattern mining; and 3) ranking.

In the first processing phase (involving clustering for co-occurring and consecutive events), for each point of time across the user history, the knowledge engine identifies the state of the human user. This state may be used, for example, to identify an activity being conducted by the human user (e.g., jogging near home before work) that occurs at a specific time (e.g., Monday morning). This is discussed below with reference to the event pattern analysis discussed below for FIGS. 3 and 4.

In the second processing phase (involving pattern mining), the knowledge engine assesses the meaningfulness and significance of each pattern discovered in the first processing phase. This pattern evaluation may be used, for example, to identify co-occurrences of events, activities, and results being performed by the human user (e.g., jogging usually occurs on Monday mornings, sometimes on weekends). This is discussed below with reference to the pattern grouping analysis discussed below for FIGS. 4 and 5.

In the third processing phase (involving ranking), the knowledge engine ranks the resulting patterns based on the meaningfulness metrics calculated in the second processing phase. This ranking may be used, for example, to identify the significance of certain patterns, along with the confidence of the certain events, activities, and results of the patterns occurring (e.g., jogging occurs during weekday mornings with a 70% confidence). This is discussed below with reference to the ranking and scoring analysis discussed below for FIG. 5.

As a further example, with use of the knowledge engine operating with the respective processing phases a consuming software application may operate to: obtain, capture, or access user information relevant to usage; operate the knowledge engine to obtain meaningful behavioral patterns; query the knowledge engine for rules concerning a specific user intent (e.g., a user state for a given intent); or query the knowledge engine for rules concerning a specific state that the user might be in (e.g., user actions/intents for a given user state).

As a first example, the knowledge engine may perform the processing to determine a state based on intent. For instance, a jogging app may provide all the user's exercise events into the knowledge engine. Given location, time, calendar events and weather, the knowledge engine may determine the most probable states in which the user is training. A consuming software application may then query the knowledge engine for recommendations on when to schedule an exercise, based on the user intrinsic preferences as inferred by past behavior.

As a second example, the knowledge engine may perform the processing to determine an intent for a given state. For instance, a personal assistant may provide information about phone calls that the user made into the knowledge engine. Then, given the present state of the user {e.g., on monday evening; at work in a meeting; later than usual to home} a personal assistant may query the knowledge engine on the likelihood that the user will call his spouse, in order to proactively offer him/her to do so.

Figure 3:
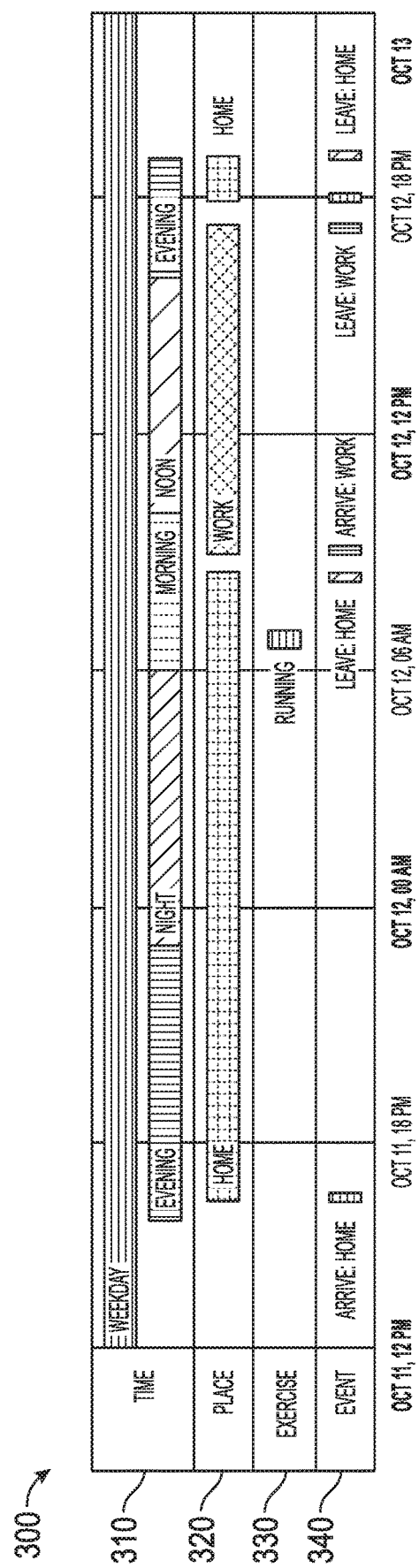
FIG. 3 illustrates a timeline of identified events processed with a knowledge engine, according to an example.

FIG. 3 illustrates an example timeline 300 of identified events processed with a knowledge engine. Specifically, the example timeline 300 depicts a timeline representation of data from a user's activities, including the visual representation of identified times 310, identified places 320, identified exercise activities 330, and identified events 340.

The example timeline 300 further illustrates the population of synthetic events in the identified events 340 categorization. For example, travel events are correlated to the identified places 320 and a known activity (e.g., "arrive: home", "leave: home". "arrive: work". "leave: work"). It will be understood that other data fields, attributes, and types may be detected and tracked for the activity of a particular human subject during a certain time scale. However, the events by themselves simply provide a data log of activity at a certain time, place, and categorization; the events depicted within the timeline 300 are not yet correlated or processed to provide actionable data contexts.

Figure 4:
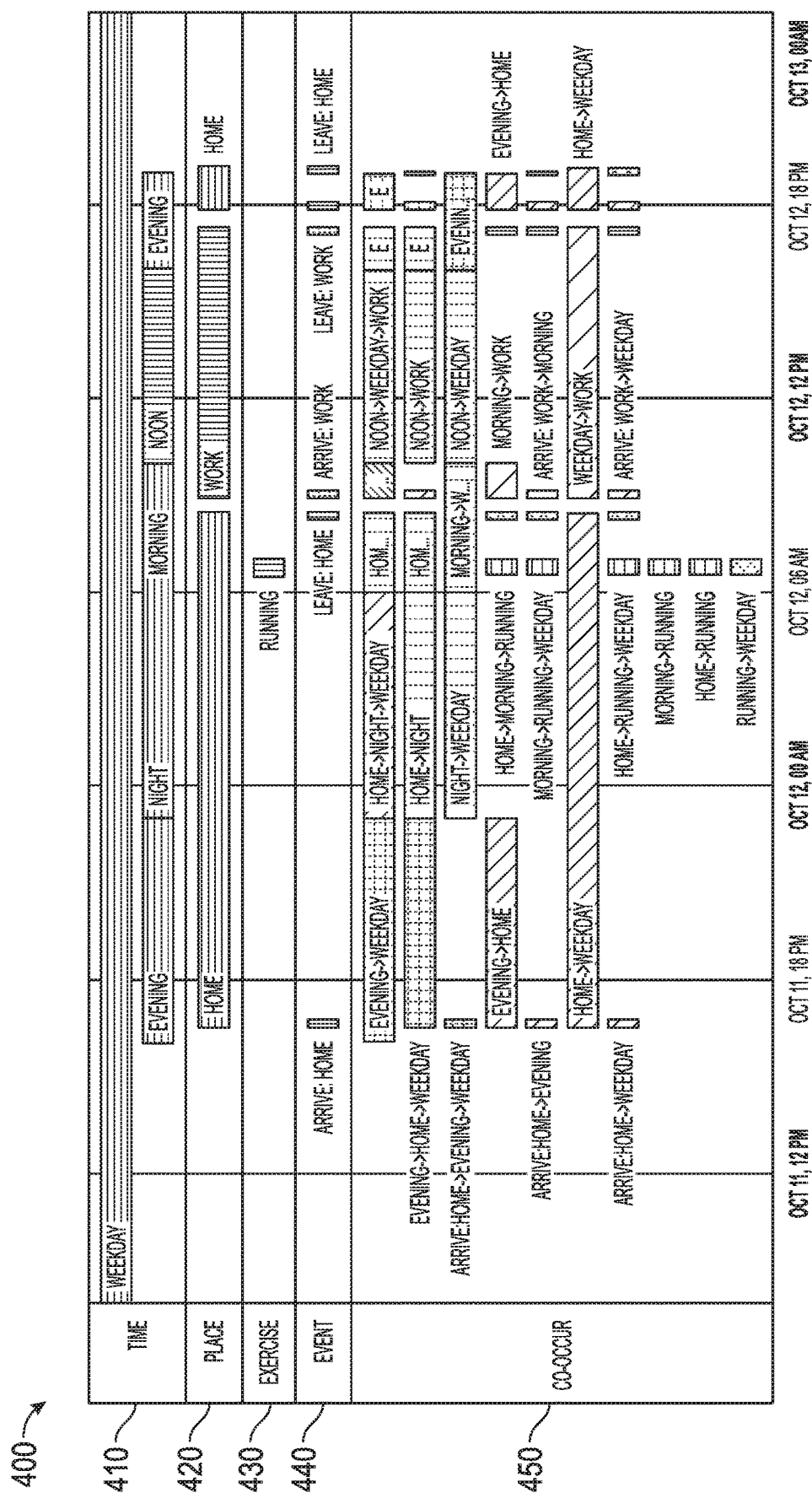
FIG. 4 illustrates a timeline of identified events and co-occurrences processed with a knowledge engine, according to an example.

FIG. 4 illustrates an example timeline 400 of identified events and co-occurrences processed with a knowledge engine. The operations of the timeline 400 include the synthetic events depicted in timeline 300 (e.g., in the similar identified times 410, identified places 420, identified exercise activities 430, and identified events 440), but with the additional identification of co-occurrence clustering 450. For example, travel events are not only correlated to the identified places 420 and a known activity (e.g., "arrive: home", "leave: home", "arrive: work", "leave: work"), but also to sequences and context of such activities (e.g., "arrive: home→evening", "morning→running→weekday").

The co-occurrence clustering 450 thus may establish useful connections between times, locations, conditions, and particular activities for a human subject (or a group of human subjects). A co-occurrence may be more precisely defined as two or more simultaneous (e.g., concurrent) events. In an example, the knowledge engine calculates all co-occurrences between two or more events in the system, for a first event that is a user intent/action and for a second event that involves one or more of a user's states.

Non-limiting examples of such co-occurrences might include:
 Running (action)↔Morning (state)
 Running (action)↔Morning (state)↔Central park (state)
 Running (action)↔Morning (state)↔Central park (state)↔Sunny (state)
 Calling mom (action)↔Weekend (state)↔Night (state)
 Arriving to work (action)↔Tuesday (state)↔Morning (state)
 Biking (action)↔Daylight (state)↔Weekday (state)↔No rain (state)

Co-occurrences may be deterministic or fuzzy. Fuzzy co-occurrences have a probability of being true. This is useful if the underlying data is noisy (for example, if 70% confident that the user is located at a restaurant, but 30% confident that the user is located at a nearby shop). The co-occurrence probability may be used when searching for the most meaningful patterns.

In an example, the co-occurrences may be created, updated, and evaluated by the knowledge engine through the use of consecutive events clustering, meaningful pattern mining, and ranking. The following paragraphs discuss aspects of these respective operations.

Consecutive Events Clustering:

In an example, part of the user's state may be defined to include events occurring prior to other events. Non-limiting examples of consecutive events might include:
 {Leaving home}→{Driving}↔{Arriving to work}
 {Leaving work}→{Calling spouse}
 {Bar-Night}→{Late to work↔Morning}

The knowledge engine may operate to perform clustering based on such identified consecutive events. As co-occurrences, consecutive events may also be fuzzy.

Meaningful Pattern Mining:

In an example, the knowledge engine aggregates and evaluates each pattern, in order to identify if the pattern is frequent and significant. As non-limiting examples of meaningful patterns:
 Calling Mom↔Weekend↔Night (17 times)
 Calling Mom↔Weekday↔At work (3 times)
 Calling Mom↔Morning (1 time)
 Calling Dad→Calling mom (2 times)

Sporadic patterns that have low support in the data may be removed at this stage.

Ranking:

In an example, the knowledge engine ranks each pattern by utilizing a scoring function comprised of one or more metrics. These metrics may be directly evaluated by the knowledge engine for aspects of event support, damped support, event confidence, density, a density factor, event significance, durational support, frequency-aware significance, or the like. The application of these metrics by the knowledge engine is further discussed below.

FIG. 5 illustrates an example ranking 500 of co-occurrences processed with a knowledge engine, such as on the data values established from the co-occurrences clustering 450 described above. The example ranking 500 is specifically illustrated as an example output of a query, looking at a longer period of time and filtering on a specific class of activities (e.g., "Running").

In the example ranking 500, a series of ranks 510 and co-occurrence listings 520, are correlated to a support ranking 530, a confidence ranking 540, and a ranking score 550. As shown, a specific co-occurrence between an event (morning) and an action (running) is detected as highest correlation, namely that a typical morning involves running.

Based on the example ranking of co-occurrences performed by the knowledge engine, various conclusions may be determined. For example, a conclusion may include, "User is expected to go running on mornings, when the weather permits." Also, a conclusion may include, "User prefers to run around Home."

In further examples, the knowledge engine employs one or more combinations of metrics for evaluating and applying ranking factors. These may include metrics of:

Event Support S(x):
Represents the number of times this co-occurrence occurred, or the sum of probabilities of this co-occurrence in case of fuzziness.

Damned Support (x,τ):
Support in the last τ days.

Event Confidence (x,τ):
Given an event (usually a user action or intent) and the underlying state, the event confidence is the number of times a co-occurrence of a specific event and its underlying state events happened, divided by the total co-occurrences of this event with other state events in the last τ days.

Density D(x,τ):
The overall duration of a state event x divided by the entire time horizon. For example, a Weekday event will have density of ~5/7. Monday Morning will have density of ~4/168 (occurs 4 hours each week). If the user is driving for two hours a day on average, the driving density would be 2/24. The model favors patterns that co-occur with smaller time windows, as these are more specific for the user.

Density Factor DF(x,τ):
is a logistic function over the density:

$$DF(x) = \frac{L}{1 + e^{-k \cdot D(x)}}$$

where L and k are smoothing parameters.

Event Significance:
Given these metrics, the knowledge engine may calculate the co-occurrence significance S(x,τ), the weighted average of the confidence, and the density factor, in the following way:

$$S(x,\tau) = \alpha \cdot C(x,\tau) + (1-\alpha)DF(x,\tau)$$

where α is determined per query.

Durational Support:
The knowledge engine may evaluate the number of times this event occurs weekly/monthly/quarterly. This assists in detecting false frequent patterns that are not due to user routines, or belong to an expired routine.

Frequency Aware Significance:
The knowledge engine may evaluate the frequency of the event in question instead of its density. Patterns may be weighted based on the uniformity of their frequency.

Given predefined thresholds for the proposed metrics, the knowledge engine may output a ranked list of probable activities. For example, the following list may be generated to detect the user's exercise patterns:

1. Running↔Monday↔Morning↔Park {sig.=0.87}
2. Running↔Wednesday↔Evening↔Gym {sig.=0.65}
3. Swimming↔Monday↔Morning↔Rain {sig.=0.6}

Using patterns ranked by significance, the knowledge engine may extract behavioral insights about the user's exercise workouts. For example, it is possible to detect that on rainy days, the trainer goes swimming instead of running. Additionally, pattern mining may be performed on the events metadata, which indicates meeting participants, calories burnt in exercise, and semantic understanding of location etc., as indicated with the following examples:

1. Running {400 calories}↔Monday↔Morning↔Park {sig. 0.94}
2. Running {800 calories}↔Evening↔Gym {sig. 0.88}
3. Meeting {participants include Jeff}↔Tuesday↔Noon↔Work {sig. 0.63}
4. Restaurant {type=Chinese}↔Holiday↔Evening {sig. 0.54}

Although many of the previous examples were provided with reference to exercise and work activity, the operation of the knowledge engine is not limited to such data. The knowledge engine may run on any discrete temporal data, such as weather, sleep, various user activities, and any state data that might affect the user behavior. In addition, the knowledge engine may process data to detect patterns on the metadata of events, such as the average calorie burn of an exercise, the participants in a meeting or the duration of a phone call.

The knowledge engine is not limited to consumption of the previously discussed forms of user activity data. The knowledge engine may generally run on any discrete temporal data, e.g., weather, sleep, various user activities, and any state data that might affect the user behavior. In addition, it may also detect patterns on the metadata of events, such as the average calorie burn of an exercise, the participants in a meeting or the duration of a phone call.

Figure 6:
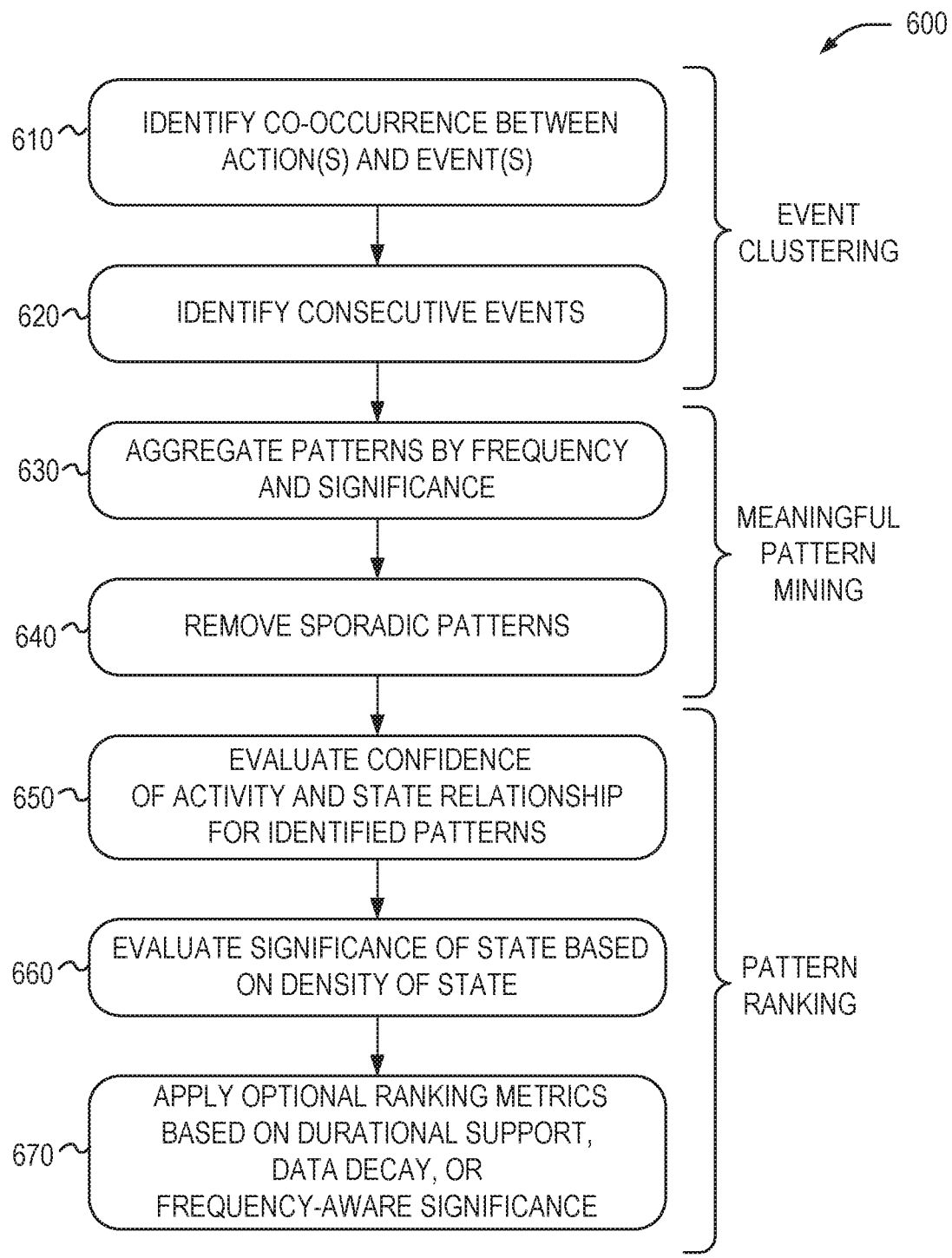
FIG. 6 illustrates a detailed operational flow for event clustering, pattern mining, and pattern ranking, for processing occurring with a knowledge engine, according to an example.

FIG. 6 illustrates another detailed operational flow 600 for event clustering, pattern mining, and pattern ranking, for processing occurring with a knowledge engine. As shown, the operational flow 600 includes a breakout of actions performed during event clustering (operations 610, 620), meaningful pattern mining (operations 630, 640), and pattern ranking (operations 650, 660, 670) on activity data. In an example, the activity data includes data obtained from at least one sensor in a personal electronic device of the human subject. In another example, the activity data includes user-generated data, and wherein the personalization action is used to predict a certain action in a software application, based on a given time or external characteristic.

As discussed in the examples herein, event clustering may include the identification of co-occurrences between one or more actions and one or more events (operation 610), and the identification of consecutive events (operation 620). In an example, the events may be identified using time, location, and activity type characteristics of the activity data. In another example, events may be identified from non-user specific data, such as weather, traffic and holidays. Such non-user specific data may also include non-location based states (such as activity level, or whether the user is out-of-office) and past states (such as sleep quality at previous night).

As also discussed in the examples herein, meaningful pattern mining may include the aggregation of patterns by frequency and significance (operation 630), and the removal of sporadic patterns (operation 640). As also discussed in the examples herein, pattern ranking may involve: the evaluation of a confidence for a particular activity-and-state relationship for one or more identified patterns (operation 650), the evaluation of significance of a state based on the density of a state (operation 660), and the application of various ranking metrics involving characteristics such as durational support, data decay, or frequency-aware significance (operation 670).

The "activity" that is being evaluated with such co-occurrences may be include a particular action the engine is trying to estimate (for example, for action prediction, discussed below), or one of the contextual traits that support a particular decision (for example, a user's current activity level). In an example, the knowledge engine may be used to answer two types of questions:

1. Action prediction: What is the most likely action given current state, e.g., argmax$_{action}$ P(action|state)
2. Pattern discovery: What is the most likely state in which the user usually performs a given action, i.e., argmax$_{state}$ P(state|action)

In an example, action prediction involves use of the knowledge engine as an action prediction engine to find the most likely action, given the current user state, and given the previously performed action and its corresponding states. Pseudo-code, given the co-occurrence mechanism discussed herein, may include operations on the following input and output:

Input:
Current state S$_{current}$, action type (e.g. exercise type), past states and actions sets S, A respectively Operations:
1. Gather base events from the data source (e.g., location, weather, activities, sleep, from a userDB)
2. Filter events given S$_{current}$ and action type
3. Assemble co-occurrence set on the filtered set.
4. Filter co-occurrences given the requested action type
5. For each distinct co-occurrence c(A; S) calculate:
   i. confidence(c)=p(a|s), a∈A, s=S
   ii. support(c)=number of times c occurred
   iii. score(c): predefined function with considerations such as preferred patterns
6. Filter out all non-significant co-occurrences (below MIN_SUPPORT or MIN_SCORE)

Output:
predicted action based on max(score) or $$\max_a \left( \sum_g \text{score}(a) \right)$$

In a further example, pattern discovery operations may be performed with a knowledge engine configured as a pattern discovery engine. The pattern discovery engine uses a similar pre-process as the action prediction engine (gathering of base events, creating co-occurrences). Following the preprocess phase, the pattern discovery engine estimates the probability of being in a state (or set of states). This probability p(state) is calculated based on the overall duration the user had been in this event divided (noted as duration(state)) by the total amount of time in which data was analyzed, T:

$$\text{duration}(e) = \sum_{i=1}^{N_e} t_{i,end} - t_{i,start}$$

Where $t_{i,end}$ and $t_{i,start}$ are the end time and start time of event i, respectively and $N_e$ is the number of events of a specific value e (e.g. all running events, all rain events).

The total analysis time frame duration may be calculated in the following manner:

$$T = \max_i(t_{i,end}) - \min_i(t_{i,start})$$

The probability calculation may be similar for any type of event (state or action):

$$p(\text{state}) = \frac{\text{duration}(\text{state})}{T}, \ p(\text{action}) = \frac{\text{duration}(\text{action})}{T}$$

Then, for each action, the engine finds the joint probability p(action, state) which resembles a co-occurrence of an action event with a state event (or multiple state events). In order to calculate this value, a co-occurring event is evaluated, which has a start time of the maximum start time of the base events, and ends at the minimum end time of the base events. The density and probability of such co-occurring event that includes events i,j,k is described below:

$$\text{density}(e_i, e_j, e_k) = \frac{\text{duration}(cooc_{e_i,e_j,e_k})}{T} = p(e_i, e_j, e_k)$$

$$p(\text{action, state}) = \text{density}(\text{action, state})$$

where state represents one or more co-occurring state events (e.g., at home in the evening while raining).

Once the prior probabilities of all events are calculated (events=actions, state events and co-occurrences between sets of events and actions) the confidence of each pattern may be calculated. In addition, the number of times the user performed an action while in this state (support) is also calculated. A pattern with a high support and high confidence is considered significant.

$$\text{Conf}(\text{state} \to \text{action}) = \frac{p(\text{state, action})}{p(\text{state})}$$

The duration of an action is sometimes not relevant. For example, the duration of a phone call may be less important than the binary information of making a phone call or not. In this case, a probability of 1/T may be assigned to each action event, and used to create a new score metric that is normalized using a time window of interest τ. This time window may be decided by the modeler and used to normalize the model towards the desired time frame in which a pattern is significant.

If the events happen on a daily basis, a time window τ=24 hours may be selected. If the event happens less or more frequently, the time window may be adjusted. The adjusted confidence may be represented by Score as follows:

$$\text{Score}(\text{state} \to \text{action}) = \text{Conf}(\text{state} \to \text{action}) * \tau$$

In a further example, to handle cases where the duration of the action event has importance (e.g., a fitness exercise in some use cases), the time window may be normalized to obtain results between 0 and 1.

Figure 7:
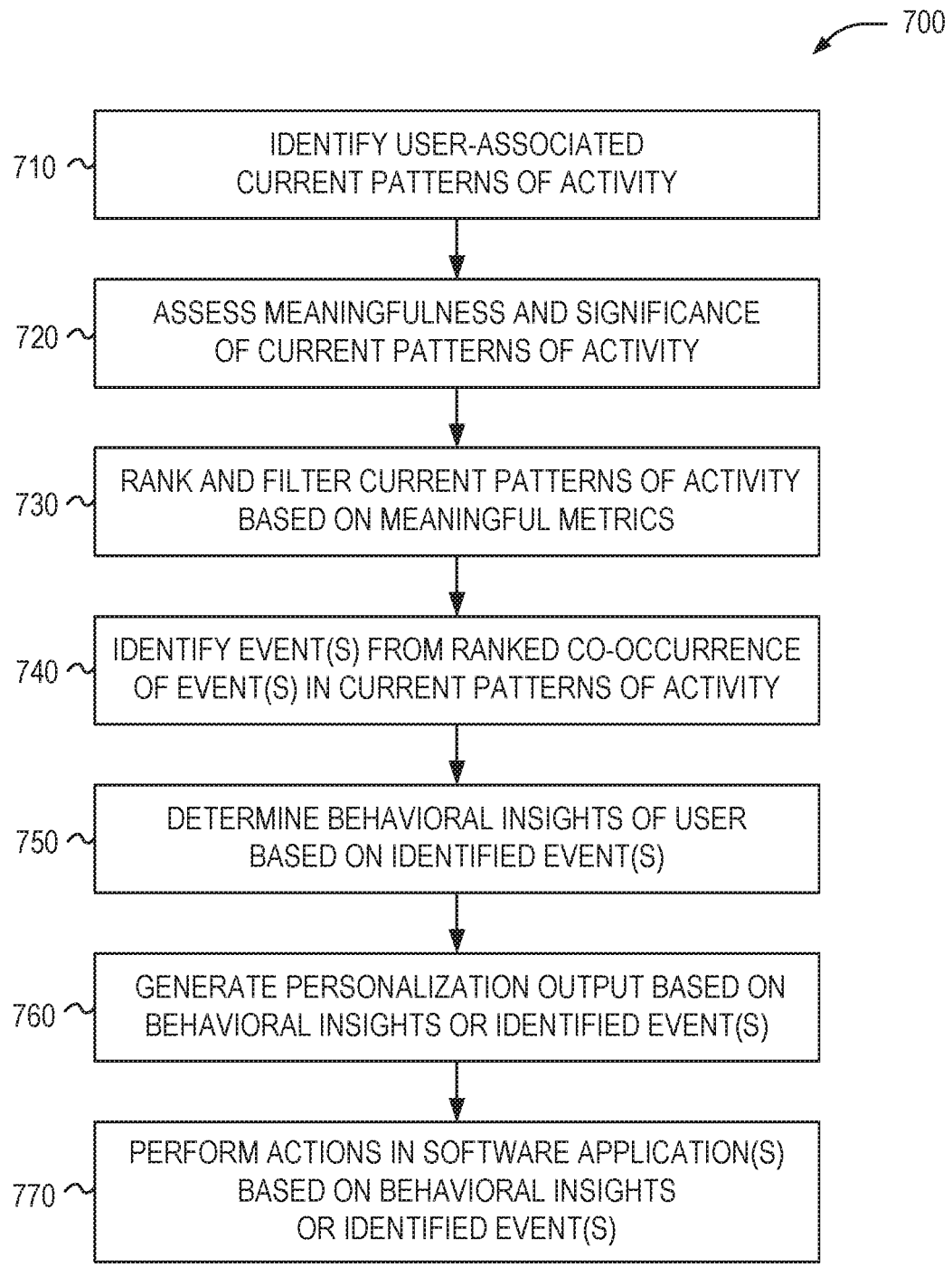
FIG. 7 illustrates a flowchart of a method for event and pattern processing occurring with a knowledge engine, for the identification of personalized events, according to an example.

FIG. 7 is a flowchart 700 illustrating an example method for event and pattern processing occurring with a knowledge engine, for the identification of personalized events. The following operations of the flowchart 700 may be conducted by an electronic processing system (including a specialized computing system) adapted to process event and activity data with the knowledge engine techniques discussed herein. It will be understood that the operations of the flowchart 700 may also be performed by other devices, including multiple devices in concert, with the sequence and type of operations of the flowchart 700 potentially modified based on the other examples of data ranking, mining, and clustering provided herein.

The operations of the flowchart 700 include the identification of user-associated current patterns of activity (operation 710) from data sources, such as data collected from sensors and logs of a computing system. The operations of the flowchart continue with the assessment of meaningfulness and significance of current patterns of activity (operation 720), along with techniques to rank and filter current patterns of activity based on meaningful metrics (operation 730). These metrics may involve any combination of data evaluation and scoring discussed above (e.g., with reference to FIGS. 4 and 5).

As a result of the pattern matching, ranking, and filtering, various events will be associated with resulting patterns. These events may be identified from ranked co-occurrences of one or multiple events (including sequences of events) in the current patterns of activity (operation 740). From these events, the knowledge engine then operates to identify and determine behavioral insights for a particular user (or set of users, activities, or events) based on the ranked groupings (operation 750). For example, a behavioral insight may include the prediction of an action, such as the prediction of what the most likely action that a user will undertake given a particular state. Likewise, a behavioral insight might include the identification of the most likely state that the user is expected to perform a certain action.

Based on the identified actions, events, patterns, and behavioral insights, various forms of personalization outputs may be provided, transmitted, or generated for a user and accompanying electronic systems (operation 760). This personalization output may be accompanied by the performance of particular actions in one or more software applications, which perform activities or procedures based on the behavioral insights or particular identified events, actions, and state combinations (operation 770). For example, the data may be consumed by smart agents, user-interactive interfaces, and "bot" software applications; prediction and data evaluation platforms; personal assistance clients and services; and the like. Respective data content may also be output from these sources with use of the personalization outputs and behavioral insights.

In a further example, the knowledge engine may be used for pattern detection of anomalies. The knowledge engine may evaluate the detected patterns as input for a routine anomaly detection of health and wellness issues, such as may be used for monitoring health issues of elderly persons. Such health issues may be detected either by directly monitoring the person's state or activity (e.g., whether the person is experiencing high blood pressure, whether the person took medicine or not, etc.), or by inspecting the person's general behavior over time. For example, if an elderly person is skipping most of his or her weekly activities or her visits to the community center, it might indicate that there is a medical issue, either physical or mental. By detecting health issues in an early stage, a caretaker or a physician may be informed of the problem, thus enabling them to act and prevent the health issue from further degradation.

Existing approaches are used only to detect high-level characteristics of a person's condition by single or aggregated measurements, such as fall detection, high glucose concentration, the number of steps walked today, and the like. These measurements are often obtained using wearable devices or smart home devices. Since many conditions cannot be detected by a single or aggregated measurements, the presently described knowledge engine may employ a detector that is capable of detecting a change in the person's routine behavior over time, even using sources that are not directly health related such as location and time in day. In an example, the knowledge engine may be used by applications of wearable device technology for a detailed behavioral analysis of an elderly person, to provide actionable insights and alerts to the user, caretaker or physician.

By observing a set of activities over time for a particular subject, it is possible to automatically detect changes in behavior that may indicate a deterioration in the subject's medical condition. The behavioral patterns, actions, and events may be inferred using a plurality of wearable and smart home sensors, located in the person's home or outside. The evaluation of this data with the knowledge engine may also be used to complement state of the art systems that already detect medical emergency situations in real time for a broader understanding of the person's condition.

For example, in the context of patterns that exist for an elderly subject, such patterns in the subject's daily life include various events occurring regularly on specific times or states. For example, such patterns may include activities performed in the morning, when outside the house, while sleeping, two to three times a week, and more. Out of routine behavior may be defined as a change in pattern over time, or a drastic change in behavior due to various factors, amongst them a change in medical condition. The knowledge engine may be used to automatically detect and respond to statistically significant patterns of the user's daily actions and states. For example:

The system detects that the elderly person usually uses the toilet once every morning. Lately, this behavior and pattern of use has changed.

The elderly person typically takes 3 pills before lunch, but hasn't done so in the last 4 days. This might indicate that a prescription needs to be refilled, or that the subject is not taking the prescription due to a sickness.

The elderly person's walking pattern is 1000 steps each evening, but lately the subject is not walking at all. This might indicate a deterioration in his body strength and general health.

Such patterns may be translated to behavioral insights and provided to the caretaker for further inspection. Thus, the knowledge engine may operate to provide a decision support system for the caretaker, who is provided with a representation of changes in the patient's life, allowing the caretaker to identify which of the changes in routine behavior are important and should be addressed.

In an example, the operation of the knowledge engine may be used in combination with devices and systems that detect and monitor health conditions. A first example of products, includes those that detect/monitor health statuses. These products are capable of detecting specific actions or states that are identifiable by sensors. For example, such products may include: Fall detection; Activity trackers (sleep, awake, walking etc.); Cardiac monitors; environment tracking devices (Light, UV, humidity, temperature, air quality); smart diapers; center of mass change detection sensors. The knowledge engine may be used to perform a longer-term behavioral analysis of the signals detected and data collected from these products. Existing devices are not able to inspect contextual traits such as the time of day, whether the person slept well at night, or whether she is in her home or not. Further, existing devices include logic that is often exclusively rule based and not evaluated in a statistical model; likewise such devices are aimed at detecting a specific condition, and not a change in the subject's overall behavior.

Thus, existing approaches are unable to: detect and identify that an adverse event (such as a fall) took place outside of a specific environment (e.g., away from home); provide insights about the fact that the person experienced multiple adverse events (e.g., fell twice as many times this month than the last); automatically detect the existence of patterns related to the signal and data that is collected; detect insights about specific locations or conditions (e.g., that the person fell twice at the staircase in the community center). Thus, existing approaches are unable to identify any other patterns that are not pre-defined as rules by developers.

In a further example, the knowledge engine may be used and consumed by products that provide personalized guidance for daily activities. For example, some devices provides elderly people with personalized guidance to complete daily life activities by analyzing their living routines. Such systems might detect, for example, that that the person is walking 500 steps, 3 times a day. Existing forms of such systems do not offer the detection of newly experienced routines, and will not provide information about out of routine behavior to the person nor to the caretaker.

Additionally, the proposed knowledge engine discussed herein may apply models that resemble association rules, data mining, and cognitive computing methods. Such models may be used in respective use cases to automatically digest multivariate sensory signals, and extract user meaningful patterns. As such, used of the presently described techniques involve fewer samples to fit a model than in existing training approaches for anomaly detection.

Figure 8:
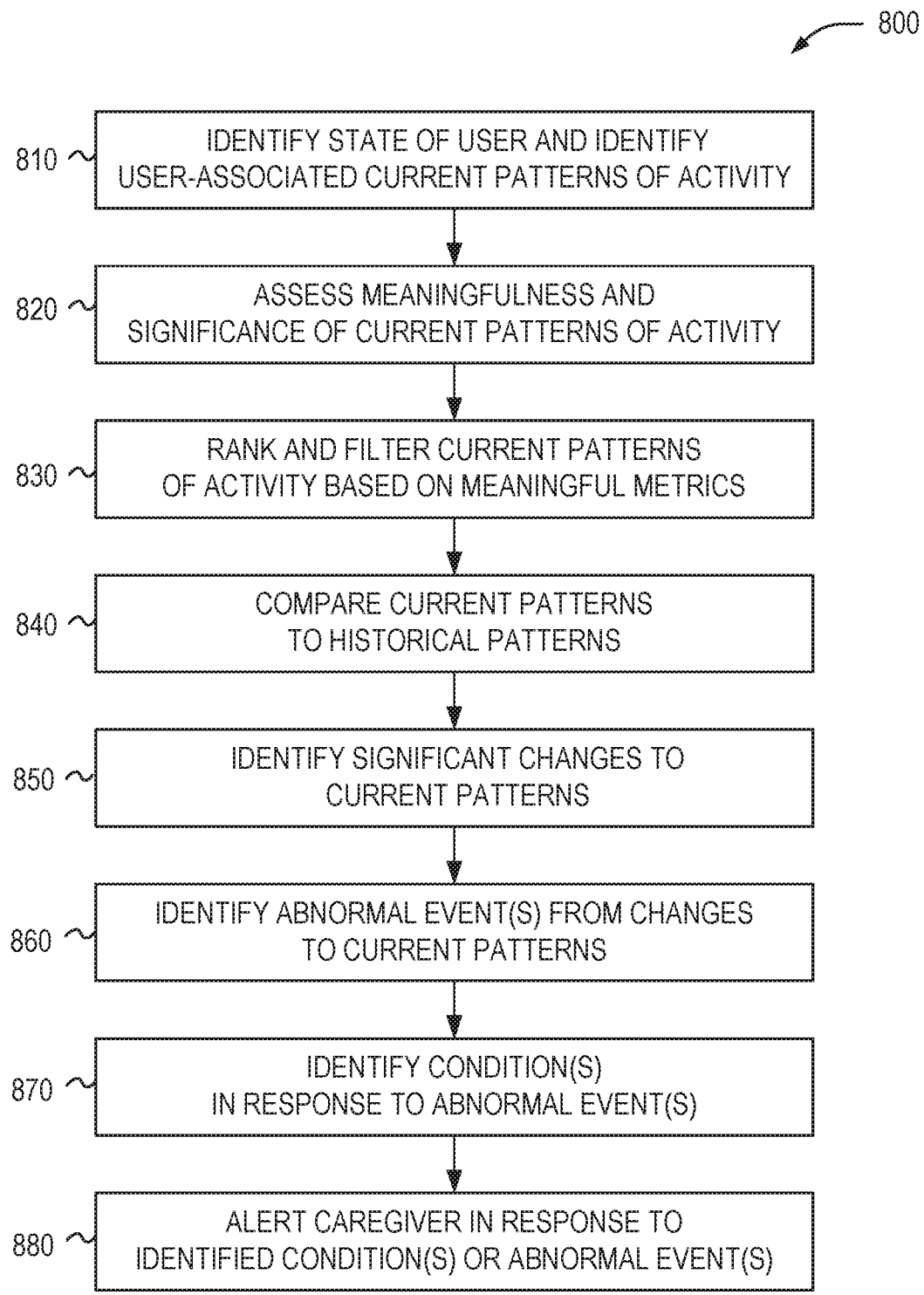
FIG. 8 illustrates a flowchart of a method for event and pattern processing occurring with a knowledge engine, for the detection of abnormal events using the knowledge engine, according to an example.

FIG. 8 is a flowchart 800 illustrating an example method of anomaly detection for a routine of a human user. Similar to FIG. 7, the operations of the flowchart 800 may be conducted by an electronic processing system (including a specialized computing system) adapted to process, generate, and output data, including in embodiments of a mobile computing device. Although the flowchart 800 and the text below depicts specific operations used for the detection of anomalies for elderly persons on behalf of a caregiver, it will be understood that the operations of the flowchart 800 may be adapted to other anomaly detection scenarios and thus may be modified based on variations to the operations.

The operations of the flowchart 800 include the identification of a state of a user and an identification of user-associated patterns (operation 810). This identification may include the analysis of current patterns of activity being performed or conducted by a human user (or human subject), or with the analysis of each point of time across the user history. The identification of one or more states and activities may be performed by the knowledge engine with the techniques described above, including the performance of co-occurring consecutive events clustering.

The operations of the flowchart 800 further include the assessment of meaningfulness and significance of current patterns (operation 820), such as may be performed through meaningful pattern mining (e.g., to assess the meaningfulness and significance of each pattern discovered from the user history). The current patterns that are identified then may be ranked and further filtered (operation 830), such as may be performed through the identification of patterns based on meaningful metrics. This ranking and filtering will be used to identify a subset of detected patterns as input for a routine anomaly detection algorithm.

The operations of the flowchart 800 to perform the anomaly detection are further based on an evaluation of current patterns to historical or expected patterns (operation 840). The evaluation may identify significant changes to current patterns, based on historical or expected patterns (operation 850). Once patterns are detected, such patterns may be evaluated over time. Any change in a significant pattern over time may indicate one or more abnormal events (operation 860), which in turn, may indicate a problem. However, in order to avoid false positives for anomalies, a supervising user (e.g., a caretaker) may define which particular signals and/or patterns are of interest.

Finally, certain identified conditions may be detected, flagged, or emphasized based on the abnormal events and anomalous patterns (operation 870). For example, if a particular activity or pattern of activities was significant for a human subject for a few weeks, and then stopped being significant, this could indicate a change in behavior that should be alerted to the caretaker for evaluation (operation 880).

As a further example, the identification of co-occurrence (e.g., in the user-associated current patterns) may be defined as two or more simultaneous events. The knowledge engine may operate to calculate all co-occurrences between two events in the system, wherein one event is a user action and the others are the user's states. Such co-occurrences, in the case of anomaly detection for elderly subjects, could include:

Walking (action)↔Morning (state)
Walking (a)↔Morning (s)↔Home (s)
Sleeping (a)↔Weekend (s)↔Night (s)
Arriving to community center (a)↔Tuesday (s)↔Morning (s)
Stationary (a)↔Morning (s)↔Weekday (s)↔Rain (s)

For each time t, the knowledge engine evaluates all subgroups of the user state, and not only the complete state. If at time t the full state was (walking, morning, Monday, weekday), then the knowledge engine collects all possible combinations of states in order to find significant subgroups as well:

[{Walking, Morning}, {Walking, Monday, Morning}, . . . ].

In addition, co-occurrence could be deterministic or fuzzy. Fuzzy co-occurrences have a probability of being true. This is useful if the underlying data is noisy (i.e. we are 70% certain that the user is at home, and 30% certain that he is at a neighbor's house). The co-occurrence probability may be used when searching for the most meaningful patterns.

As a further example, the identification of consecutive events clustering for anomaly detection with elderly subjects may evaluate the user's state for events occurring prior to other events. For example, consecutive events could include:

{Leaving home}→{Driving}→{Arriving to community center}
{Sleeping 9 hours}→{Walking 30 minutes}
{Sleep 5 hours↔Night}→{Not walking↔Morning}

As in co-occurrences, consecutive events may also be fuzzy, and subsets of consecutive states are considered as well.

As a further example, the identification of meaningful pattern mining for anomaly detection with elderly subjects may include the knowledge engine operating to aggregate and evaluate each pattern, in order to identify if this pattern is frequent and significant (meaningful). For example, meaningful patterns relevant to activity of elderly persons may include:

Taking pills↔Weekend↔Night (17 times)
Taking pills↔Weekday↔At home (12 times)
Walking↔Morning (1 time)
Sleep 9 hours→Walking 30 minutes (2 times)

Sporadic patterns that have low support in the data may be removed at this stage. As a further example, the ranking of patterns for anomaly detection with elderly subjects may include the knowledge engine operating to automatically rank each pattern by utilizing different ranking metrics. Such ranking metrics may include:

Ranking Based on Confidence:

For example, evaluate how many times this activity occurred in that state vs. in other states. Where I=Intent; S=State (Either time: morning, weekend, holiday; or state: At home, around work, in a meeting, after a full night sleep), then:

Confidence=$P(I \cap S)/P(S)$

Ranking Based on Significance:

In order to prefer find grained states (Morning vs. Weekday), the knowledge engine may operate to estimate the density of each state. In an example, density may be determined by:

$$\text{Density} = \sum_{s \in S} \text{duration}_s/(\text{overall time period})$$

For example, a weekday would receive ~5/7 and a Monday morning would receive ~4/168 since it occurs for 4 hours a week. In an example, significance may be determined by Significance$(s)$=Confidence$_s$*(1−density$_s$)

Additional metrics may include: (a) Durational support, to evaluate the number of times this event occurs weekly/monthly/quarterly (this assists in finding frequent patterns that are out of routines, or belong to an expired routine), (b) Significance given data decay (to increase weight of closer events in order to support dynamics in behavior); and (c) Frequency aware significance (to use the frequency of the event in question instead of its density, where patterns are weighted based on the uniformity of their frequency.)

Given predefined thresholds for the proposed metrics, the knowledge engine may output a list of probable activities. For example, in order to detect the user's exercise patterns:

1. Exercising↔Monday↔Morning↔Home {sig.=0.87}
2. Not Exercising↔Wednesday↔Evening↔Rain {sig.=0.65}
3. Exercising↔Monday↔Morning↔No Rain {sig.=0.6}

Given this information, the knowledge engine may extract behavioral insights about the user's activity. For example, it is possible to detect that on rainy days, the elderly person does not perform any physical activity. Once patterns are detected, they may be evaluated over time. Any change in a significant pattern over time might indicate a problem. However, in order to avoid false alarms, the caretaker may define which signals and/or patterns are of interest. For example, if a pattern was significant for a few weeks, and then stopped being significant, this could indicate a change in behavior that should be evaluated by the caretaker.

Figure 9:
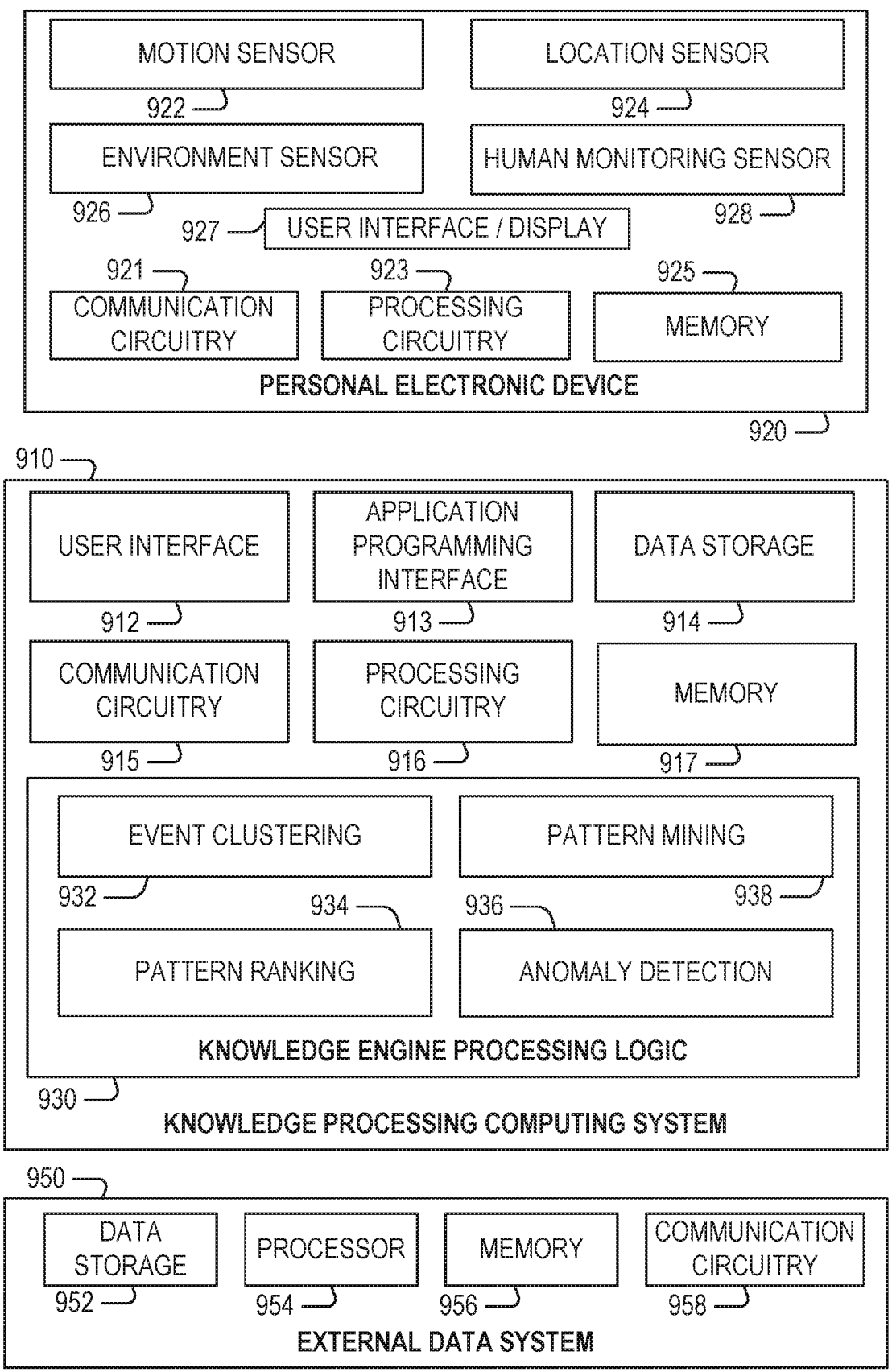
FIG. 9 illustrates a block diagram of components in a system for implementation and utilization of a knowledge engine, according to an example.

FIG. 9 illustrates a block diagram of components in an example system implementation and utilization of a knowledge engine, based on the knowledge engine processing techniques discussed herein. As shown, the block diagram depicts a knowledge processing computing system 910 (e.g., a computing system) that is adapted to implement features of the knowledge engine through knowledge engine processing logic 930, a personal electronic device 920 to collect input data relating to a human subject that is consumed and processed by the knowledge engine, and an external data system 950 used to store and collect data used by and in connection with the knowledge engine. As discussed below, the knowledge processing computing system 910 includes circuitry and interfaces (described below) to facilitate the operation of the knowledge engine, including for features of the operations depicted in operation flows and flowcharts 200, 600, 700, and 800.

The knowledge processing computing system 910 is depicted as including: circuitry to implement a user interface 912, e.g., to output or facilitate an interactive user interface that allows user interaction with the knowledge engine features); circuitry to implement an application programming interface 913 to communicate data with and perform operations for consuming software applications of the knowledge engine, such as those operated by the personal electronic device 920, and the external data system 950; data storage 914 to store rules, instructions, and other data for operation and use of the knowledge engine; communication circuitry 915 to communicate with an external network or devices via wired or wireless networking components; and processing circuitry 916 (e.g., a CPU) and a memory 917 (e.g., volatile or non-volatile memory) used to perform electronic operations for use and operation of the knowledge engine and related aspects of knowledge processing computing system 910. In an example, the knowledge engine processing logic 930 may operate with specialized hardware operating independent from the processing circuitry 916 and the memory 917; in other examples, the knowledge engine processing logic 930 may be software-configured hardware that is implemented with use of the processing circuitry 916 and the memory 917 (e.g., by instructions executed by the processing circuitry 916 and the memory 917).

In the knowledge processing computing system 910, the user interface 912 may be used to output a command and control interface for a respective user (who may or may not be the human subject that is evaluated with the knowledge engine). The user interface 912 also may be used to control operations and initiate actions with the knowledge engine processing logic 930. In other examples, the operation and interaction with the knowledge engine may occur via the application programming interface 913, such as with the receipt of commands and queries from respective software agents (including software agents operating on the personal electronic device). The knowledge engine processing logic 930 is depicted as including event clustering 932 to perform the evaluation, sorting, and grouping of events or event types related to a human subject; pattern ranking 934 to perform an ordering, assessment, or evaluation of identified patterns of events related to a human subject; pattern mining 938 to locate and identify co-occurrences of patterns and events related to a human subject; anomaly detection 936 to identify activities, events, patterns, and actions that are abnormal (and that may provide actionable intelligence for a caretaker or other supervisor of the subject user). The knowledge engine processing logic 930 and the knowledge processing computing system 910 may also include other components, not depicted, for implementation of other forms of the knowledge engine processing operations discussed herein.

The personal electronic device 920 is depicted as including: a motion sensor 922 to capture data indicative of motion of a human subject; a location sensor 924 to capture data indicative of a geographic or relative location of a human subject; an environment sensor 926 to capture characteristics of the environment that surround the human subject; a human monitoring sensor 928 to capture other personal (e.g., physiological) attributes or characteristics of the human subject and the human subject's activity. The personal electronic device 920 is further depicted as including a user interface and display unit 927 to allow display and control of data features (such as may be provided through software user interfaces that include output of information from the knowledge engine processing logic; processing circuitry 923 and memory 925 to execute instructions and perform relevant actions that collect data and output data for the human subject via the user interface and display unit 927; and communication circuitry 921 to receive and send information relevant to the human subject, knowledge engine queries, sensor data, and the like. In an example, the knowledge processing computing system 910 (e.g., a mobile computing device) is a physically separate device from the personal electronic device 920 (e.g., a wearable device); in other examples, the knowledge processing computing system 910 and one or more of the operational components of the personal electronic device 920 are integrated into the same device, for example, into an advanced wearable device (e.g., smart watch) or into a mobile computing device (e.g., smart phone) providing a user interface, display, processing circuitry, in addition to a number of sensors.

The external data system 950 is depicted as including: a data storage 952 to store data such as identified patterns, events, personal data, or supplemental content used for evaluation by the knowledge engine processing logic 930; processing circuitry 954 and memory 956 to execute software instructions to capture, record, sort, and analyze the patterns, events, personal data, or supplemental content, such as in response to a request from the knowledge processing computing system 910; and communication circuitry 958 to send and receive data for the patterns, events, personal data, or supplemental content, such as to transmit the supplemental data in response to the request from the knowledge processing computing system 910. In some examples, the external data system 950 is operated as a remote server that provides data and processing on-demand; in other examples, the data storage and data processing features of the external data system 950 may be integrated into or coordinated with the knowledge processing computing system 910.

Figure 10:
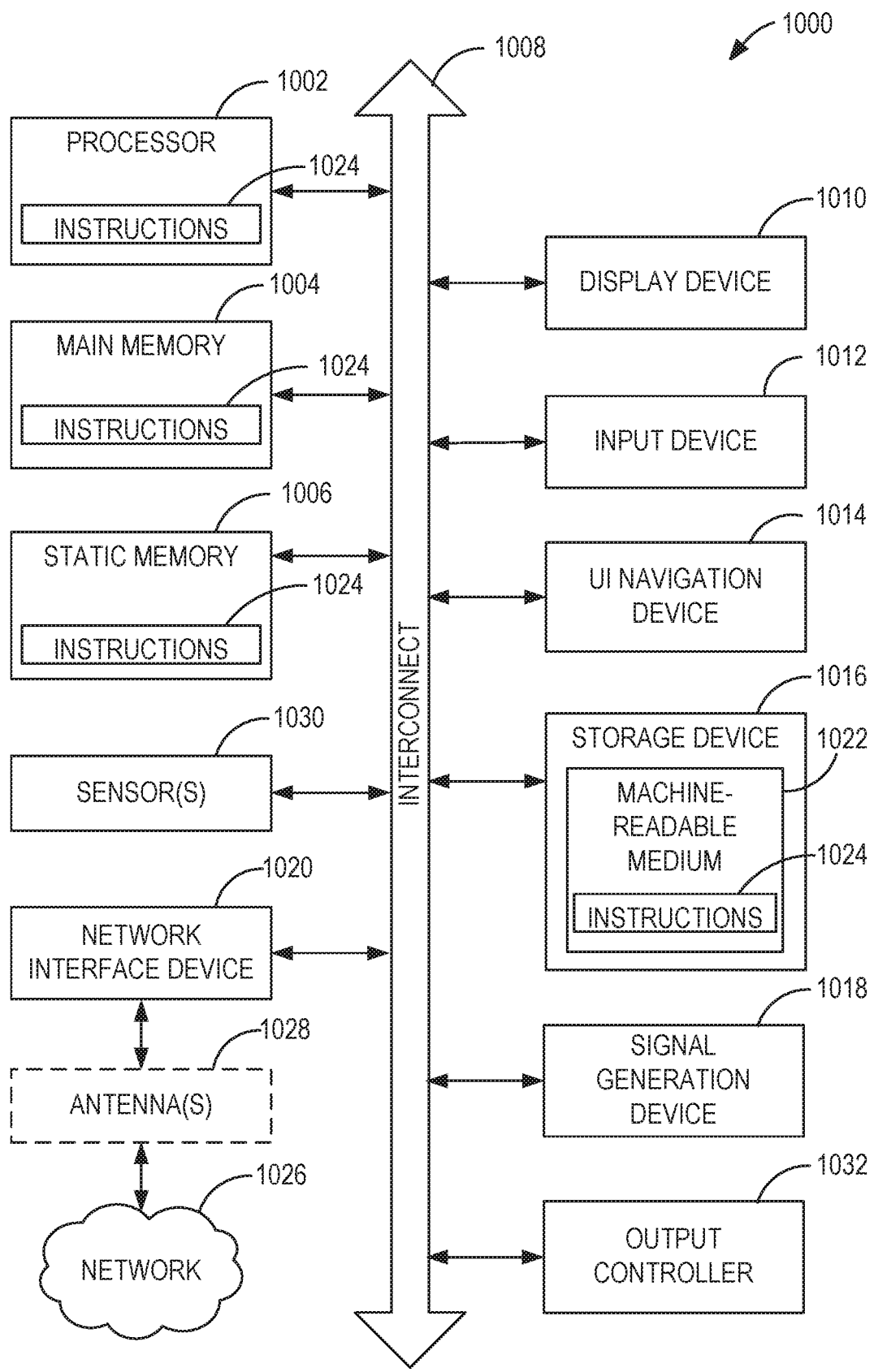
FIG. 10 illustrates a block diagram for an example electronic processing system upon which any one or more of the techniques (e.g., operations, processes, methods, and methodologies) discussed herein may be performed, according to an example.

FIG. 10 is a block diagram illustrating a machine in the example form of an electronic processing system 1000, within which a set or sequence of instructions may be executed to cause the machine to perform any one of the methodologies discussed herein, according to an example embodiment. The machine may be a personal computer (PC), a tablet PC, a personal digital assistant (PDA), a mobile telephone or smartphone, smart watch or integrated wearable computing device, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein. Similarly, the term "processor-based system" shall be taken to include any set of one or more machines that are controlled by or operated by a processor (e.g., a computer) to individually or jointly execute instructions to perform any one or more of the methodologies discussed herein.

Example electronic processing system 1000 includes at least one processor 1002 (e.g., a central processing unit (CPU), a graphics processing unit (GPU) or both, processor cores, compute nodes, etc.), a main memory 1004 and a static memory 1006, which communicate with each other via an interconnect 1008 (e.g., a link, a bus, etc.). The electronic processing system 1000 may further include a video display unit 1010, an input device 1012 (e.g., an alphanumeric keyboard), and a user interface (UI) control device 1014 (e.g., a mouse, button controls, etc.). In one embodiment, the video display unit 1010, input device 1012 and UI navigation device 1014 are incorporated into a touch screen display. The electronic processing system 1000 may additionally include a storage device 1016 (e.g., a drive unit), a signal generation device 1018 (e.g., a speaker), an output controller 1032 (e.g., for control of actuators, motors, and the like), a network interface device 1020 (which may include or operably communicate with one or more antennas 1030, transceivers, or other wireless communications hardware), and one or more sensors 1026 (e.g., cameras), such as a global positioning system (GPS) sensor, compass, accelerometer, location sensor, or other sensor.

The storage device 1016 includes a machine-readable medium 1022 on which is stored one or more sets of data structures and instructions 1024 (e.g., software) embodying or utilized by any one or more of the methodologies or functions described herein. The instructions 1024 may also reside, completely or at least partially, within the main memory 1004, static memory 1006, and/or within the processor 1002 during execution thereof by the electronic processing system 1000, with the main memory 1004, static memory 1006, and the processor 1002 also constituting machine-readable media.

While the machine-readable medium 1022 is illustrated in an example embodiment to be a single medium, the term "machine-readable medium" may include a single medium or multiple media (e.g., a centralized or distributed database, and/or associated caches and servers) that store the one or more instructions 1024. The term "machine-readable medium" shall also be taken to include any tangible medium that is capable of storing, encoding or carrying instructions for execution by the machine and that cause the machine to perform any one or more of the methodologies of the present disclosure or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including but not limited to, by way of example, semiconductor memory devices (e.g., electrically programmable read-only memory (EPROM), electrically erasable programmable read-only memory (EEPROM)) and flash memory devices; magnetic disks such as internal hard disks and removable disks; magneto-optical disks; and CD-ROM and DVD-ROM disks.

The instructions 1024 may further be transmitted or received over a communications network 1028 using a transmission medium via the network interface device 1020 utilizing any one of a number of transfer protocols (e.g., HTTP). Examples of communication networks include a local area network (LAN), a wide area network (WAN), the Internet, mobile telephone networks, plain old telephone (POTS) networks, and wireless data networks (e.g., Wi-Fi, 2G/3G, and 4G LTE/LTE-A, or other personal area, local area, or wide area networks). The term "transmission medium" shall be taken to include any intangible medium that is capable of storing, encoding, or carrying instructions for execution by the machine, and includes digital or analog communications signals or other intangible medium to facilitate communication of such software.

Embodiments used to facilitate and perform the techniques described herein may be implemented in one or a combination of hardware, firmware, and software. Embodiments may also be implemented as instructions stored on a machine-readable storage device, which may be read and executed by at least one processor to perform the operations described herein. A machine-readable storage device may include any non-transitory mechanism for storing information in a form readable by a machine (e.g., a computer). For example, a machine-readable storage device may include read-only memory (ROM), random-access memory (RAM), magnetic disk storage media, optical storage media, flash-memory devices, and other storage devices and media.

It should be understood that the functional units or capabilities described in this specification may have been referred to or labeled as components or modules, in order to more particularly emphasize their implementation independence. Such components may be embodied by any number of software or hardware forms. For example, a component or module may be implemented as a hardware circuit comprising custom very-large-scale integration (VLSI) circuits or gate arrays, off-the-shelf semiconductors such as logic chips, transistors, or other discrete components. A component or module may also be implemented in programmable hardware devices such as field programmable gate arrays, programmable array logic, programmable logic devices, or the like. Components or modules may also be implemented in software for execution by various types of processors. An identified component or module of executable code may, for instance, comprise one or more physical or logical blocks of computer instructions, which may, for instance, be organized as an object, procedure, or function. Nevertheless, the executables of an identified component or module need not be physically located together, but may comprise disparate instructions stored in different locations which, when joined logically together, comprise the component or module and achieve the stated purpose for the component or module.

Indeed, a component or module of executable code may be a single instruction, or many instructions, and may even be distributed over several different code segments, among different programs, and across several memory devices or processing systems. In particular, some aspects of the described process (such as pattern mining operations of the knowledge engine) may take place on a different processing system (e.g., in a computer in a data center), than that in which the code is deployed (e.g., in a client computer providing an interface to the knowledge engine). Similarly, operational data may be identified and illustrated herein within components or modules, and may be embodied in any suitable form and organized within any suitable type of data structure. The operational data may be collected as a single data set, or may be distributed over different locations including over different storage devices, and may exist, at least partially, merely as electronic signals on a system or network. The components or modules may be passive or active, including agents operable to perform desired functions.

Additional examples of the presently described method, system, and device embodiments include the following, non-limiting configurations. Each of the following non-limiting examples may stand on its own, or may be combined in any permutation or combination with any one or more of the other examples provided below or throughout the present disclosure.

Example 1 is a device for generating personalized output from pattern recognition and prediction, the device comprising processing circuitry to: identify, from activity data of the human subject, patterns of activity using clustering of events, wherein the events are identified using time, location, and activity type characteristics of the activity data; identify, from the patterns of activity, meaningful patterns of activity, wherein the meaningful patterns of activity are identified based on co-occurrence of the time, location, and activity type characteristics for respective events; rank the identified meaningful patterns of activity, wherein the meaningful patterns of activity are ranked based on confidence and support of respective patterns to occur for the human subject with the co-occurrence of the time, location, and activity type; generate a personalization action for a software application based on the ranking of the identified meaningful patterns of activity; and perform the personalization action in the software application.

In Example 2, the subject matter of Example 1 optionally includes wherein the personalization action generated for the software application includes an action prediction, to identify a most likely action given a particular state of the human subject, and wherein the software application operates to identify the particular state of the human subject.

In Example 3, the subject matter of any one or more of Examples 1-2 optionally include wherein the personalization action generated for the software application includes a pattern discovery, to identify a most likely state in which the human subject performs a particular activity, and wherein the software application operates to identify the particular activity.

In Example 4, the subject matter of any one or more of Examples 1-3 optionally include wherein operations to identify the patterns of activity, from the activity data of the human subject, include pre-processing of the events to remove data values not relevant to a class of activities, wherein the clustering of the events is performed on the pre-processed events.

In Example 5, the subject matter of any one or more of Examples 1-4 optionally include wherein operations to identify the patterns of activity, from the activity data of the human subject, include creation of synthetic events from contextual evaluation of the time, location, and activity type characteristics of the activity data, wherein the clustering of the events is performed on the synthetic events.

In Example 6, the subject matter of any one or more of Examples 1-5 optionally include wherein the events are further identified using at least one of: activity information that is not specific to a particular user, an activity state that is not specific to a particular location, or historical activity data.

In Example 7, the subject matter of any one or more of Examples 1-6 optionally include the processing circuitry further to: filter the patterns of activity, wherein the meaningful patterns of activity are further identified from a filtered subset of the patterns of activity having activities that match a pre-defined characteristics of a class of activities.

In Example 8, the subject matter of any one or more of Examples 1-7 optionally include the processing circuitry further to: perform ranking of the identified meaningful patterns of activity based on at least one metric applied to respective activities in the patterns of activity, the at least one metric determined from at least one of: event support for a co-occurrence, damped support for a co-occurrence over a defined period of time, event confidence for a co-occurrence over a defined period of time, density of the event for a co-occurrence over a defined period of time, a density factor for a co-occurrence, an event significance for a co-occurrence, a durational support for a co-occurrence, or a frequency-aware significance for a co-occurrence.

In Example 9, the subject matter of any one or more of Examples 1-8 optionally include the processing circuitry further to: obtain, from an external data source, the activity data of the human subject.

In Example 10, the subject matter of any one or more of Examples 1-9 optionally include wherein the activity data includes data obtained from at least one sensor in a personal electronic device of the human subject.

In Example 11, the subject matter of any one or more of Examples 1-10 optionally include wherein the activity data includes user-generated data, and wherein the personalization action is used to predict a certain action in a software application, based on a given time or external characteristic.

In Example 12, the subject matter of any one or more of Examples 1-11 optionally include wherein operations to perform the personalization action in the software application include operations to generate a graphical output of the personalization action in the software application, wherein the graphical output of the personalization action includes an indication of an action prediction, a pattern discovery, or a pattern discovery.

In Example 13, the subject matter of any one or more of Examples 1-12 optionally include wherein the personalization action generated for the software application includes an anomaly detection, to identify an unexpected action of the human subject given a particular state of the human subject, wherein software application operates to identify the particular state of the human subject.

In Example 14, the subject matter of any one or more of Examples 11-13 optionally include wherein operations to perform the personalization action in the software application include operations to transmit a communication to a supervising human, wherein the communication to the supervising human indicates the unexpected action of the human subject.

In Example 15, the subject matter of any one or more of Examples 11-14 optionally include wherein the anomaly detection relates to the anomaly detection of a physiological or mental state of the human subject, wherein the human subject is an elderly person.

Example 16 is at least one machine readable storage medium, comprising a plurality of instructions adapted for generating personalized output from activity of a human subject, from pattern recognition and prediction, wherein the instructions, responsive to being executed with processor circuitry of a machine, cause the machine to perform operations that: identify, from activity data of the human subject, patterns of activity using clustering of events, wherein the events are identified using time, location, and activity type characteristics of the activity data; identify, from the patterns of activity, meaningful patterns of activity, wherein the meaningful patterns of activity are identified based on co-occurrence of the time, location, and activity type characteristics for respective events; rank the identified meaningful patterns of activity, wherein the meaningful patterns of activity are ranked based on confidence and support of respective patterns to occur for the human subject with the co-occurrence of the time, location, and activity type; generate a personalization action for a software application based on the ranking of the identified meaningful patterns of activity; and perform the personalization action in the software application.

In Example 17, the subject matter of Example 16 optionally includes wherein the personalization action generated for the software application includes an action prediction, to identify a most likely action given a particular state of the human subject, and wherein the software application operates to identify the particular state of the human subject.

In Example 18, the subject matter of any one or more of Examples 16-17 optionally include wherein the personalization action generated for the software application includes a pattern discovery, to identify a most likely state in which the human subject performs a particular activity, and wherein the software application operates to identify the particular activity.

In Example 19, the subject matter of any one or more of Examples 16-18 optionally include wherein operations to identify the patterns of activity, from the activity data of the human subject, include pre-processing of the events to remove data values not relevant to a class of activities, wherein the clustering of the events is performed on the pre-processed events.

In Example 20, the subject matter of any one or more of Examples 16-19 optionally include wherein operations to identify the patterns of activity, from the activity data of the human subject, include creation of synthetic events from contextual evaluation of the time, location, and activity type characteristics of the activity data, wherein the clustering of the events is performed on the synthetic events.

In Example 21, the subject matter of any one or more of Examples 16-20 optionally include wherein the events are further identified using at least one of: activity information that is not specific to a particular user, an activity state that is not specific to a particular location, or historical activity data.

In Example 22, the subject matter of any one or more of Examples 16-21 optionally include wherein the instructions further cause the machine to perform operations that: filter the patterns of activity, wherein the meaningful patterns of activity are further identified from a filtered subset of the patterns of activity having activities that match a pre-defined characteristics of a class of activities.

In Example 23, the subject matter of any one or more of Examples 16-22 optionally include wherein the instructions further cause the machine to perform operations that: perform ranking of the identified meaningful patterns of activity based on at least one metric applied to respective activities in the patterns of activity, the at least one metric determined from at least one of: event support for a co-occurrence, damped support for a co-occurrence over a defined period of time, event confidence for a co-occurrence over a defined period of time, density of the event for a co-occurrence over a defined period of time, a density factor for a co-occurrence, an event significance for a co-occurrence, a durational support for a co-occurrence, or a frequency-aware significance for a co-occurrence.

In Example 24, the subject matter of any one or more of Examples 16-23 optionally include wherein the instructions further cause the machine to perform operations that: obtain, from an external data source, the activity data of the human subject.

In Example 25, the subject matter of any one or more of Examples 16-24 optionally include wherein the activity data includes data obtained from at least one sensor in a personal electronic device of the human subject.

In Example 26, the subject matter of any one or more of Examples 16-25 optionally include wherein the activity data includes user-generated data, and wherein the personalization action is used to predict a certain action in a software application, based on a given time or external characteristic.

In Example 27, the subject matter of any one or more of Examples 16-26 optionally include wherein operations to perform the personalization action in the software application include operations to generate a graphical output of the personalization action in the software application, wherein the graphical output of the personalization action includes an indication of an action prediction, a pattern discovery, or a pattern discovery.

In Example 28, the subject matter of any one or more of Examples 16-27 optionally include wherein the personalization action generated for the software application includes an anomaly detection, to identify an unexpected action of the human subject given a particular state of the human subject, wherein software application operates to identify the particular state of the human subject.

In Example 29, the subject matter of Example 28 optionally includes wherein operations to perform the personalization action in the software application include operations to transmit a communication to a supervising human, wherein the communication to the supervising human indicates the unexpected action of the human subject.

In Example 30, the subject matter of any one or more of Examples 28-29 optionally include wherein the anomaly detection relates to the anomaly detection of a physiological or mental state of the human subject, wherein the human subject is an elderly person.

Example 31 is a system for generating personalized output from pattern recognition and prediction, comprising: a knowledge processing computing system, comprising processing circuitry and memory to execute instructions for generating personalized output from activity of a human subject, the instructions to perform operations that: identify, from activity data of the human subject, patterns of activity using clustering of events, wherein the events are identified using time, location, and activity type characteristics of the activity data; identify, from the patterns of activity, meaningful patterns of activity, wherein the meaningful patterns of activity are identified based on co-occurrence of the time, location, and activity type characteristics for respective events; rank the identified meaningful patterns of activity, wherein the meaningful patterns of activity are ranked based on confidence and support of respective patterns to occur for the human subject with the co-occurrence of the time, location, and activity type; and generate a personalization action for a software application based on the ranking of the identified meaningful patterns of activity; wherein the personalization action generated for the software application includes: an action prediction to identify a most likely action given a particular state of the human subject, or a pattern discovery to identify a most likely state in which the human subject performs a particular activity.

In Example 32, the subject matter of Example 31 optionally includes a personal electronic device, comprising: at least one sensor to capture at least a portion of the activity data; communication circuitry to communicate the at least a portion of the activity data to the knowledge processing computing system; and processing circuitry and memory to execute instructions that cause a selection and a transmission of the activity data, in response to a request from the knowledge processing computing system.

In Example 33, the subject matter of any one or more of Examples 31-32 optionally include an external data system, comprising: data storage to store the activity data; communication circuitry to communicate the activity data to the knowledge processing computing system; and processing circuitry and memory to execute instructions that cause a selection and a transmission of the activity data, in response to a request from the knowledge processing computing system.

Example 34 is a method of generating personalized output from pattern recognition and prediction, the method comprising electronic operations including: identifying, from activity data of the human subject, patterns of activity using clustering of events, wherein the events are identified using time, location, and activity type characteristics of the activity data; identifying, from the patterns of activity, meaningful patterns of activity, wherein the meaningful patterns of activity are identified based on co-occurrence of the time, location, and activity type characteristics for respective events; ranking the identified meaningful patterns of activity, the ranking performed based on confidence and support of respective patterns to occur for the human subject with the co-occurrence of the time, location, and activity type; generating a personalization action for a software application based on the ranking of the identified meaningful patterns of activity; and performing the personalization action in the software application.

In Example 35, the subject matter of Example 34 optionally includes wherein the personalization action generated for the software application includes an action prediction, to identify a most likely action given a particular state of the human subject, and wherein the software application operates to identify the particular state of the human subject.

In Example 36, the subject matter of any one or more of Examples 34-35 optionally include wherein the personalization action generated for the software application includes a pattern discovery, to identify a most likely state in which the human subject performs a particular activity, and wherein the software application operates to identify the particular activity.

In Example 37, the subject matter of any one or more of Examples 34-36 optionally include wherein identifying the patterns of activity, from the activity data of the human subject, includes pre-processing of the events to remove data values not relevant to a class of activities, wherein the clustering of the events is performed on the pre-processed events.

In Example 38, the subject matter of any one or more of Examples 34-37 optionally include wherein identifying the patterns of activity, from the activity data of the human subject, includes creation of synthetic events from contextual evaluation of the time, location, and activity type characteristics of the activity data, wherein the clustering of the events is performed on the synthetic events.

In Example 39, the subject matter of any one or more of Examples 34-38 optionally include wherein the events are further identified using at least one of: activity information that is not specific to a particular user, an activity state that is not specific to a particular location, or historical activity data.

In Example 40, the subject matter of any one or more of Examples 34-39 optionally include electronic operations including: filtering the patterns of activity, wherein the meaningful patterns of activity are further identified from a filtered subset of the patterns of activity having activities that match a pre-defined characteristics of a class of activities.

In Example 41, the subject matter of any one or more of Examples 34-40 optionally include electronic operations including: performing ranking of the identified meaningful patterns of activity based on at least one metric applied to respective activities in the patterns of activity, the at least one metric determined from at least one of: event support for a co-occurrence, damped support for a co-occurrence over a defined period of time, event confidence for a co-occurrence over a defined period of time, density of the event for a co-occurrence over a defined period of time, a density factor for a co-occurrence, an event significance for a co-occurrence, a durational support for a co-occurrence, or a frequency-aware significance for a co-occurrence.

In Example 42, the subject matter of any one or more of Examples 34-41 optionally include electronic operations including: obtaining, from an external data source, the activity data of the human subject.

In Example 43, the subject matter of any one or more of Examples 34-42 optionally include wherein the activity data includes data obtained from at least one sensor in a personal electronic device of the human subject.

In Example 44, the subject matter of any one or more of Examples 34-43 optionally include wherein the activity data includes user-generated data, and wherein the personalization action is used to predict a certain action in a software application, based on a given time or external characteristic.

In Example 45, the subject matter of any one or more of Examples 34-44 optionally include wherein performing the personalization action in the software application includes generating a graphical output of the personalization action in the software application, wherein the graphical output of the personalization action includes an indication of an action prediction, a pattern discovery, or a pattern discovery.

In Example 46, the subject matter of any one or more of Examples 34-45 optionally include wherein the personalization action generated for the software application includes an anomaly detection, to identify an unexpected action of the human subject given a particular state of the human subject, wherein software application operates to identify the particular state of the human subject.

In Example 47, the subject matter of Example 46 optionally includes wherein performing the personalization action in the software application include transmitting a communication to a supervising human, wherein the communication to the supervising human indicates the unexpected action of the human subject.

In Example 48, the subject matter of any one or more of Examples 40-47 optionally include wherein the anomaly detection relates to the anomaly detection of a physiological or mental state of the human subject, wherein the human subject is an elderly person.

Example 49 is at least one machine readable medium including instructions, which when executed by a computing system, cause the computing system to perform any of the methods of Examples 34-48.

Example 50 is an apparatus comprising means for performing any of the methods of Examples 34-48.

Example 51 is an apparatus, comprising: means for identifying, from activity data of a human subject, patterns of activity using clustering of events, wherein the events are identified using time, location, and activity type characteristics of the activity data; means for identifying, from the patterns of activity, meaningful patterns of activity, wherein the meaningful patterns of activity are identified based on co-occurrence of the time, location, and activity type characteristics for respective events; means for ranking the identified meaningful patterns of activity, the ranking performed based on confidence and support of respective patterns to occur for the human subject with the co-occurrence of the time, location, and activity type; means for generating a personalization action for a software application based on the ranking of the identified meaningful patterns of activity; and means for performing the personalization action in the software application.

In Example 52, the subject matter of Example 51 optionally includes means for generating the personalization action for the software application with an action prediction, to identify a most likely action given a particular state of the human subject, and wherein the software application operates to identify the particular state of the human subject.

In Example 53, the subject matter of any one or more of Examples 51-52 optionally include means for generating the personalization action for the software application with a pattern discovery, to identify a most likely state in which the human subject performs a particular activity, and wherein the software application operates to identify the particular activity.

In Example 54, the subject matter of any one or more of Examples 51-53 optionally include means for pre-processing of the events to remove data values not relevant to a class of activities, wherein clustering of the events is performed on the pre-processed events.

In Example 55, the subject matter of any one or more of Examples 51-54 optionally include means for creating synthetic events from contextual evaluation of the time, location, and activity type characteristics of the activity data, wherein clustering of the events is performed on the synthetic events.

In Example 56, the subject matter of any one or more of Examples 51-55 optionally include means for further identifying the events using at least one of: activity information that is not specific to a particular user, an activity state that is not specific to a particular location, or historical activity data.

In Example 57, the subject matter of any one or more of Examples 51-56 optionally include means for filtering the patterns of activity, wherein the meaningful patterns of activity are further identified from a filtered subset of the patterns of activity having activities that match a pre-defined characteristics of a class of activities.

In Example 58, the subject matter of any one or more of Examples 51-57 optionally include means for performing ranking of the identified meaningful patterns of activity based on at least one metric applied to respective activities in the patterns of activity, the at least one metric determined from at least one of: event support for a co-occurrence, damped support for a co-occurrence over a defined period of time, event confidence for a co-occurrence over a defined period of time, density of the event for a co-occurrence over a defined period of time, a density factor for a co-occurrence, an event significance for a co-occurrence, a durational support for a co-occurrence, or a frequency-aware significance for a co-occurrence.

In Example 59, the subject matter of any one or more of Examples 51-58 optionally include means for obtaining, from an external data source, the activity data of the human subject.

In Example 60, the subject matter of any one or more of Examples 51-59 optionally include wherein the activity data includes data obtained from at least one sensor in a personal electronic device of the human subject.

In Example 61, the subject matter of any one or more of Examples 51-60 optionally include means for evaluating the activity data, wherein the activity data includes user-generated data, and wherein the personalization action is used to predict a certain action in a software application, based on a given time or external characteristic.

In Example 62, the subject matter of any one or more of Examples 51-61 optionally include means for generating a graphical output of the personalization action in the software application, wherein the graphical output of the personalization action includes an indication of an action prediction, a pattern discovery, or a pattern discovery.

In Example 63, the subject matter of any one or more of Examples 51-62 optionally include means for generating the personalization action for the software application based on an anomaly detection, to identify an unexpected action of the human subject given a particular state of the human subject, wherein software application operates to identify the particular state of the human subject.

In Example 64, the subject matter of Example 63 optionally includes means for transmitting a communication to a supervising human, wherein the communication to the supervising human indicates the unexpected action of the human subject.

In Example 65, the subject matter of any one or more of Examples 63-64 optionally include wherein the anomaly detection relates to the anomaly detection of a physiological or mental state of the human subject, wherein the human subject is an elderly person.

Example 66 is a system configured to perform operations of any one or more of Examples 1-65.

Example 67 is a method for performing operations of any one or more of Examples 1-65.

Example 68 is a machine readable medium including instructions that, when executed by a machine cause the machine to perform the operations of any one or more of Examples 1-65.

Example 69 is a system comprising means for performing the operations of any one or more of Examples 1-65.

In the above Detailed Description, various features may be grouped together to streamline the disclosure. However, the claims may not set forth every feature disclosed herein as embodiments may feature a subset of said features. Further, embodiments may include fewer features than those disclosed in a particular example. Thus, the following claims are hereby incorporated into the Detailed Description, with a claim standing on its own as a separate embodiment.

What is claimed is:

1. A device for generating personalized output from pattern recognition and prediction, the device comprising processing circuitry to:
   identify, from activity data of a human subject, patterns of activity using clustering of events, wherein the events are identified using time, location, and activity type characteristics of the activity data;
   identify, from the patterns of activity, meaningful patterns of activity, wherein the meaningful patterns of activity are identified based on co-occurrence of the time, location, and activity type characteristics for respective events;
   rank the identified meaningful patterns of activity, wherein the meaningful patterns of activity are ranked based on confidence and support of respective patterns to occur for the human subject with the co-occurrence of the time, location, and activity type;
   identify at least two of the identified meaningful patterns of activity are within a predefined range of confidence;
   receive temporal data from a source independent of the human subject based on identifying that there are at least two of the identified meaningful patterns of activity within a predefined range of confidence;
   adjust the ranking of the at least two identified meaningful patterns of activity based on the temporal data;
   calculate a significance score for each of the at least two identified meaningful patterns of activity, the significance score represented by a weighted average of the confidence and a density factor of a meaningful pattern of activity, wherein the density factor is a logistic function over a density of an event, the density of an event representing an overall duration of an event divided by a related time horizon;
   filter patterns from the at least two identified meaningful patterns of activity that have a significance score that is less than a threshold significance score, to produce a filtered set of meaningful patterns of activity;
   generate a personalization action for a software application based on the ranking of the filtered set of meaningful patterns of activity; and
   perform the personalization action in the software application.

2. The device of claim 1, wherein the personalization action generated for the software application includes an action prediction to identify a most likely action given a particular state of the human subject, and wherein the software application operates to identify the particular state of the human subject.

3. The device of claim 1, wherein the personalization action generated for the software application includes a pattern discovery to identify a most likely state in which the human subject performs a particular activity, and wherein the software application operates to identify the particular activity.

4. The device of claim 1, wherein operations to identify the patterns of activity, from the activity data of the human subject, include pre-processing of the events to remove data values not relevant to a class of activities, wherein the clustering of the events is performed on the pre-processed events.

5. The device of claim 1, wherein operations to identify the patterns of activity, from the activity data of the human subject, include creation of synthetic events from contextual evaluation of the time, location, and activity type characteristics of the activity data, wherein the clustering of the events is performed on the synthetic events.

6. The device of claim 1, wherein the events are further identified using at least one of: activity information that is not specific to a particular user, an activity state that is not specific to a particular location, or historical activity data.

7. The device of claim 1, the processing circuitry further to:
   filter the patterns of activity, wherein the meaningful patterns of activity are further identified from a filtered subset of the patterns of activity having activities that match a pre-defined characteristics of a class of activities.

8. The device of claim 1, the processing circuitry further to:
   perform ranking of the identified meaningful patterns of activity based on at least one metric applied to respective activities in the patterns of activity, the at least one metric determined from at least one of: event support for a co-occurrence, damped support for a co-occurrence over a defined period of time, event confidence for a co-occurrence over a defined period of time, density of the event, for a co-occurrence over a defined period of time, a density factor for a co-occurrence, an event significance for a co-occurrence, a durational support for a co-occurrence, or a frequency-aware significance for a co-occurrence.

9. The device of claim 1, the processing circuitry further to:
obtain, from an external data source, the activity data of the human subject.

10. The device of claim 1, wherein the activity data includes data obtained from at least one sensor in a personal electronic device of the human subject.

11. The device of claim 1, wherein the activity data includes user-generated data, and wherein the personalization action is used to predict a certain action in a software application, based on a given time or external characteristic.

12. The device of claim 1, wherein operations to perform the personalization action in the software application include operations to generate a graphical output of the personalization action in the software application, wherein the graphical output of the personalization action includes an indication of an action prediction, a pattern discovery, or a pattern discovery.

13. The device of claim 1, wherein the personalization action generated for the software application includes an anomaly detection to identify an unexpected action of the human subject given a particular state of the human subject, wherein software application operates to identify the particular state of the human subject.

14. The device of claim 13, wherein operations to perform the personalization action in the software application include operations to transmit a communication to a supervising human, wherein the communication to the supervising human indicates the unexpected action of the human subject, and wherein the anomaly detection relates to the anomaly detection of a physiological or mental state of the human subject.

15. At least one non-transitory machine readable storage medium, comprising a plurality of instructions adapted for generating personalized output from activity of a human subject, from pattern recognition and prediction, wherein the instructions, responsive to being executed with processor circuitry of a machine, cause the machine to perform operations that:
identify, from activity data of the human subject, patterns of activity using clustering of events, wherein the events are identified using time, location, and activity type characteristics of the activity data;
identify, from the patterns of activity, meaningful patterns of activity, wherein the meaningful patterns of activity are identified based on co-occurrence of the time, location, and activity type characteristics for respective events;
rank the identified meaningful patterns of activity, wherein the meaningful patterns of activity are ranked based on confidence and support of respective patterns to occur for the human subject with the co-occurrence of the time, location, and activity type;
identify at least two of the identified meaningful patterns of activity are within a predefined range of confidence;
receive temporal data from a source independent of the human subject based on identifying that there are at least two of the identified meaningful patterns of activity within a predefined range of confidence;
adjust the ranking of the at least two identified meaningful patterns of activity based on the temporal data;
calculate a significance score for each of the at least two identified meaningful patterns of activity, the significance score represented by a weighted average of the confidence and a density factor of a meaningful pattern of activity, wherein the density factor is a logistic function over a density of an event, the density of an event representing an overall duration of an event divided by a related time horizon;
filter patterns from the at least two identified meaningful patterns of activity that have a significance score that is less than a threshold significance score, to produce a filtered set of meaningful patterns of activity;
generate a personalization action for a software application based on the ranking of the filtered set of meaningful patterns of activity; and
perform the personalization action in the software application.

16. The non-transitory machine readable storage medium of claim 15, wherein the personalization action generated for the software application includes an action prediction to identify a most likely action given a particular state of the human subject, and wherein the software application operates to identify the particular state of the human subject.

17. The non-transitory machine readable storage medium of claim 15, wherein the personalization action generated for the software application includes a pattern discovery to identify a most likely state in which the human subject performs a particular activity, and wherein the software application operates to identify the particular activity.

18. The non-transitory machine readable storage medium of claim 15, wherein operations to identify the patterns of activity, from the activity data of the human subject, include creation of synthetic events from contextual evaluation of the time, location, and activity type characteristics of the activity data, wherein the clustering of the events is performed on the synthetic events.

19. The non-transitory machine readable storage medium of claim 15, wherein the instructions further cause the machine to perform operations that:
filter the patterns of activity, wherein the meaningful patterns of activity are further identified from a filtered subset of the patterns of activity having activities that match a pre-defined characteristics of a class of activities.

20. The non-transitory machine readable storage medium of claim 15, wherein the instructions further cause the machine to perform operations that:
perform ranking of the identified meaningful patterns of activity based on at least one metric applied to respective activities in the patterns of activity, the at least one metric determined from at least one of:
event support for a co-occurrence, damped support for a co-occurrence over a defined period of time, event confidence for a co-occurrence over a defined period of time, density of the event for a co-occurrence over a defined period of time, a density factor for a co-occurrence, an event significance for a co-occurrence, a durational support for a co-occurrence, or a frequency-aware significance for a co-occurrence.

21. A method of generating personalized output from pattern recognition and prediction, the method comprising electronic operations including:
identifying, from activity data of a human subject, patterns of activity using clustering of events, wherein the events are identified using time, location, and activity type characteristics of the activity data;
identifying, from the patterns of activity, meaningful patterns of activity, wherein the meaningful patterns of activity are identified based on co-occurrence of the time, location, and activity type characteristics for respective events;

ranking the identified meaningful patterns of activity, the ranking performed based on confidence and support of respective patterns to occur for the human subject with the co-occurrence of the time, location, and activity type;

identifying at least two of the identified meaningful patterns of activity are within a predefined range of confidence;

receiving temporal data from a source independent of the human subject based on identifying that there are at least two of the identified meaningful patterns of activity within a predefined range of confidence;

adjusting the ranking of the at least two identified meaningful patterns of activity based on the temporal data;

calculating a significance score for each of the at least two identified meaningful patterns of activity, the significance score represented by a weighted average of the confidence and a density factor of a meaningful pattern of activity, wherein the density factor is a logistic function over a density of an event, the density of an event representing an overall duration of an event divided by a related time horizon;

filtering patterns from the at least two identified meaningful patterns of activity that have a significance score that is less than a threshold significance score, to produce a filtered set of meaningful patterns of activity;

generating a personalization action for a software application based on the ranking of the filtered set of meaningful patterns of activity; and performing the personalization action in the software application.

22. The method of claim 21, wherein the personalization action generated for the software application includes an action prediction to identify a most likely action given a particular state of the human subject, and wherein the software application operates to identify the particular state of the human subject.

23. The method of claim 21, Therein the personalization action generated for the software application includes a pattern discovery to identify a most likely state in which the human subject performs a particular activity, and wherein the software application operates to identify the particular activity.

24. The method of claim 21, the method further comprising electronic operations including:

filtering the patterns of activity, wherein the meaningful patterns of activity are further identified from a filtered subset of the patterns of activity having activities that match a pre-defined characteristics of a class of activities.

25. The method of claim 21, the method further comprising electronic operations including:

performing ranking of the identified meaningful patterns of activity based on at least one metric applied to respective activities in the patterns of activity, the at least one metric determined from at least one of: event support for a co-occurrence, damped support for a co-occurrence over a defined period of time, event confidence for a co-occurrence over a defined period of time, density of the event for a co-occurrence over a defined period of time, a density factor for a co-occurrence, an event significance for a co-occurrence, a durational support for a co-occurrence, or a frequency-aware significance for a co-occurrence.

* * * * *

UNITED STATES PATENT AND TRADEMARK OFFICE
CERTIFICATE OF CORRECTION

PATENT NO. : 11,256,998 B2
APPLICATION NO. : 15/414387
DATED : February 22, 2022
INVENTOR(S) : Mendels et al.

It is certified that error appears in the above-identified patent and that said Letters Patent is hereby corrected as shown below:

In the Claims

In Column 28, Line 65, in Claim 8, delete "event," and insert --event-- therefor In Column 32, Line 5, in Claim 23, delete "Therein" and insert --wherein-- therefor Signed and Sealed this
Twenty-fourth Day of May, 2022

*Katherine Kelly Vidal*

Katherine Kelly Vidal
*Director of the United States Patent and Trademark Office*